(12) United States Patent
Lichtenhan et al.

(10) Patent No.: US 6,660,823 B1
(45) Date of Patent: Dec. 9, 2003

(54) MODIFYING POSS COMPOUNDS

(75) Inventors: Joseph D. Lichtenhan, San Juan Capistrano, CA (US); Frank J. Feder, Costa Mesa, CA (US); Daravong Soulivong, Lyons (FR)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 134 days.

(21) Appl. No.: 09/709,783

(22) Filed: Nov. 14, 2000

Related U.S. Application Data

(63) Continuation-in-part of application No. 09/258,248, filed on Feb. 25, 1999, now abandoned.
(60) Provisional application No. 60/076,817, filed on Mar. 3, 1998.

(51) Int. Cl.[7] .............................................. C08G 77/38
(52) U.S. Cl. ............................... 528/37; 528/9; 556/10; 556/403; 556/408; 556/409; 556/452; 556/459; 556/460

(58) Field of Search .......................... 528/9, 37; 556/10, 556/403, 408, 409, 452, 459, 460

(56) References Cited

U.S. PATENT DOCUMENTS 5,589,562 A * 12/1996 Lichtenhan et al. ........... 528/9

* cited by examiner

*Primary Examiner*—Margaret G. Moore
(74) *Attorney, Agent, or Firm*—Thomas C. Stover

(57) ABSTRACT

Method is provided for controlling the stereo chemistry of functionalities or X groups to exo or endo positions on a polyhedral oligomeric silsesquioxane (POSS) compound by adding certain reagents to said X groups to change one or more positions thereof to endo or exo. Also provided are the POSS species formed by the above inventive method. Method is also provided for inserting a ring substituent into a POSS compound. Also provided are the POSS species formed by such inventive method.

21 Claims, No Drawings

MODIFYING POSS COMPOUNDS

DOMESTIC PRIORITY

This CIP application claims the benefit of parent application, Ser. No. 09/258,248, filed in the USPTO on Feb. 25, 1999 and now abandoned, in the name of the inventors herein as well as provisional application No. 60/076,817, filed Mar. 3, 1998.

STATEMENT OF GOVERNMENT INTEREST

The invention described herein may be manufactured and used by or for the Government for governmental purposes without the payment of any royalty thereon.

BACKGROUND OF THE INVENTION

1. Field of the Invention

This invention relates to modifying polyhedral oligomeric silsesquioxane (POSS) compounds, particularly methods for controlling the stereo chemistry of functionalities or X groups to desired positions on POSS compounds and also to methods for inserting one or more ring substituents, other than silicon, into a POSS compound.

2. Description of Related Art

Recent art in the silsesquioxane field has taught processes for the chemical manipulation of the organic functionalities (substituents, e.g., denoted by R) contained on the silicon oxygen frameworks of polyhedral oligomeric silsesquioxanes (POSS). While these methods are highly useful for varying the organic functionalities contained on POSS molecules, they do not offer the ability to cleave and/or manipulate the silicon-oxygen frameworks of such compounds. Thus, these methods are of no utility for transforming the multitude of readily available polyhedral oligomeric silsesquioxanes systems into useful compounds that can be subsequently utilized for a multitude of catalysis and material applications.

Earlier art has reported that bases (e.g. NaOH, KOH, etc.) could be used to (1) catalyze the polymerization of polyhedral oligomeric silsesquioxanes into partly networked resins, (2) convert polysilsesquioxane resins into discrete polyhedral oligomeric silsesquioxane structures and (3) catalyze the redistribution of selected fully condensed polyhedral oligomeric silsesquioxane structures into other related fully condensed polyhedral oligomeric silsesquioxane structural types. While the base assisted/catalyzed method does afford the manipulation of silicon-oxygen frameworks, it is not effective at selectively producing incompletely condensed frameworks from completely condensed species. This limitation results from the intolerance of the silicon-oxygen framework present in polyhedral oligomeric silsesquioxanes to base.

Accordingly there is need and market for a method for opening and/or substituting on POSS rings that overcomes the above prior art shortcomings.

There has now been discovered a method that rapidly and effectively opens the silicon-oxygen frameworks of POSS compounds to produce species that can subsequently be converted to various functionalized POSS compounds.

SUMMARY OF THE INVENTION

Broadly the present invention provides a method for controlling the stereo chemistry of X groups to exo or endo positions on a polyhedral oligomeric silsesquioxane (POSS) compound including, adding reagents selected from the group of a) $CF_3SO_3H$ then $H_2O$, b) $Me_3SnOH$ then HCl aq. and c) $HBF_4/BF_3$ then $Me_3SnOH$ then HCl aq, to the X groups to change one or more positions thereof to endo or exo, wherein the POSS compound is of the formula $[(RSiO_{1.5})_m(RXSiO_{1.0})_n]_{\Sigma\#}$, n=4–24, m=1–12, #=m+n, R is aliphatic, aromatic, olefinic, alkoxy, siloxy or H and the X groups are selected from the type of OH, $OSO_2$ $CF_3$, $OSO_2CH_3$, F, Cl, I, Br, $Me_3SnO$, alkoxy and siloxy. Also provided are the POSS species formed by the above inventive method.

The invention further provides a method for inserting a ring substituent into a polyhedral oligomeric silsesquioxane (POSS) compound to produce a formula of the type $[(RSiO1.5)_m(RSiO_{1.0})_n(E)_j]_{\Sigma\#}$. This includes, reacting $[(RSiO_{1.5})_m(RXSiO_{1.0})_n]_{\Sigma\#}$, with a reagent selected from the group of $H_2NR$, $RB(OH)_2$, $K_2CrO_4$, $R_4NHSO_4$ and $H_2PR$ to obtain at least one expanded POSS ring in $[(RSiO_{1.5})_m(RSiO_{1.0})_n(E)_j]_{\Sigma\#}$, where n is 4–24, m is 1–12, j is 1–8, # is m+n+j, R is aliphatic, aromatic, olefinic, alkoxy, siloxy or H, X is selected from the group of $OSO_2CF_3$, $OSNMe_3$, OH, $OSO_2Cl$, $OSO_2CH_3$, $OS_3H$ and halide and E is a ring substituent replacement for oxygen selected from the group of NR, PR, $CrO_4$, $SO_4$, $O_2BR$, $O_2PR$ and $O_2P(O)R$. Also provided are the POSS species formed by such inventive method.

Definition of Molecular Representations for POSS Nanostructures

For the purposes of explaining this invention's processes and chemical compositions the following definition for representations of nanostructural-cage formulas is made:

Polysilsesquioxanes are materials represented by the formula $[RSiO_{1.5}]_\infty$ where ∞=degree of polymerization within the material and R=organic substituent (H, cyclic or linear aliphatic or aromatic groups that may additionally contain reactive functionalities such as alcohols, esters, amines, ketones, olefins, ethers or halides). Polysilsesquioxanes may be either homoleptic or heteroleptic. Homoleptic systems contain only one type of R group while heteroleptic systems contain more than one type of R group.

POSS nanostructure compositions are represented by the formula:

$[(RSiO_{1.5})_n]_{\Sigma\#}$ for homoleptic compositions $[(RSiO_{1.5})_m(RSiO_{1.5})_n]_{\Sigma\#}$ for heteroleptic compositions $[(RSiO_{1.5})_m(RXSiO_{1.0})_n]_{\Sigma\#}$ for functionalized heteroleptic compositions $[(RSiO_{1.5})_m(RSiO_{1.0})_n(E)_j]_{\Sigma\#}$ for heterofunctionalized heteroleptic compositions $[(XSiO_{1.5})]_{\Sigma\#}$ for homoleptic silicate compositions In all of the above R is the same as defined above and X includes OH, Cl, Br, I, alkoxide (OR), acetate (OOCR), peroxide (OOR), amine ($NR_2$) isocyanate (NCO), and R. The symbol E refers to elements within the composition that include (silanes and silicones e.g. $SiR_2$, $SiR_2OSiR_2OSiR_2$), (metals and nonmetals e.g. $CrO_2$, $PO_2$, $SO_2$, NR) The symbols m, n and j refer to the stoichiometry of the composition. The symbol $\Sigma$ indicates that the composition forms a nanostructure and the symbol # refers to the number of silicon atoms contained within the nanostructure. The value for # is usually the sum of m+n or m+n+j. It should be noted that $\Sigma\#$ is not to be confused as a multiplier for determining stoichiometry, as it merely describes the overall nanostructural characteristics of the POSS system (aka cage size).

By "strong acid", as used herein, is meant one with a pKa number ranging from −7 to 5 and is inclusive of superacids which cannot be assigned pKa values but which are characterized by Hammett acidity values $H_0$ that range from 30 to 2.0 with the preferred range being 8–16.

Thus the present invention discloses methods that enable the selective manipulation of the silicon-oxygen frameworks in polyhedral oligomeric silsesquioxane (POSS) cage molecules. It is desired to selectively manipulate the frameworks of POSS compounds because they are useful as intermediate chemical agents that can be further converted or incorporated into a wide variety of chemical feed-stocks useful for the preparation of catalyst supports, monomers, and polymers wherein they impart new and improved thermal, mechanical and physical properties to common polymeric materials.

Further the present invention teaches processes that enable the manipulation of the silicon-oxygen frameworks (the cage-like structure) of common polyhedral oligomeric silsesquioxane (POSS) compounds $[(RSiO_{1.5})_n]_{\Sigma\#}$ (where R=aliphatic, aromatic, olefinic, alkoxy, siloxy or H and n=4–24) into new POSS species bearing frameworks with functionalities (e.g. silanes, silylhalides, silanols, silylamines, organohalides, alcohols, alkoxides, amines, cyanates, nitriles, olefins, epoxides, organoacids, esters, and strained olefins) for grafting, polymerization, or catalysis reactions.

Also in contrast to the prior art, the invention provides for the development of acid catalyzed processes that rapidly and effectively open the silicon-oxygen frameworks of polyhedral oligomeric silsesquioxanes to produce species that can subsequently be converted into stable incompletely condensed POSS-silanol and related functionalized POSS compounds. The use of acid reagents is desirable because the silicon-oxygen frameworks in polyhedral oligomeric silsesquioxanes are more tolerant of acids and hence will not as readily polymerize to form random networks, ladder polymers or other resinous systems. Acid reagents are also desirable in that their selectivity, rate of action, and the extent of reaction with fully condensed silicon-oxygen frameworks can be controlled through concentration, acid strengths (pH), and the chemical nature of the acid and its conjugate base. The nature of the solvent medium can also impart control over the cage opening process. Manipulation of these process variables allows for the optimization of conditions by which the silicon-oxygen frameworks of polyhedral oligomeric silsesquioxanes such as $[(RSiO_{1.5})_n]_{\Sigma\#}$ (where R=aliphatic, aromatic, olefinic, alkoxy or siloxy or H and n=4–24) can be selectively manipulated to produce new polyhedral oligomeric silsesquioxanes with functionalized structures. The polyhedral oligomeric silsesquioxanes produced from the acid treatment processes can be used directly as reagents in polymerizations or they can be additionally derivatized through reaction with a variety of organosilanes or organic reagents such as amines, phosphines, transition metals, or tin complexes to form diverse new POSS chemical reagents.

Thus processes for the selective ring opening, stereochemical interconversion, expansion and reduction of the silicon oxygen frameworks in polyhedral oligomeric silsesquioxanes (POSS) to form new polyhedral oligomeric silsesquioxane chemical species have been developed. The selective ring-opening and stereochemical interconversion processes principally utilize strong acids (e.g., $HBF_4/BF_3$, $CF_3SO_3H$ (trifluoromethanesulfonic acid), $ClSO_3H$ (chlorosulfonic acid), $CH_3SO_3H$ (methanesulfonic acid), $H_2SO_4$ (sulfuric acid), $HClO_4$ (perchloric acid), etc.) to react with the silicon-oxygen-silicon framework's (Si—O—Si) bonds. Conditions in the processes can be controlled so that the Si—O—Si frameworks are selectively cleaved to afford species containing Si—X bonds where X is the conjugate base of the respective strong acid (e.g., X=F, $CF_3SO_3$, $ClSO_3$, $HSO_4$, $ClO_4$) or where X=OH. The resulting new polyhedral oligomeric silsesquioxane species can then undergo additional chemical manipulations, such as cage expansion or reduction to ultimately be converted into POSS-species bearing one or more functionalities suitable for polymerization reactions.

DETAILED DESCRIPTION OF THE INVENTION

Examples of openable POSS systems are shown below.

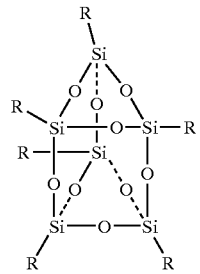

$[(RSiO_{1.5})_6]\Sigma 6$

Formula 1

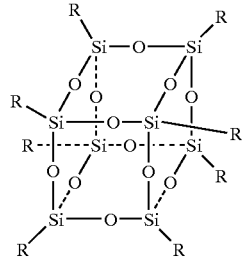

$[(RSiO_{1.5})_8]\Sigma 8$

Formula 2

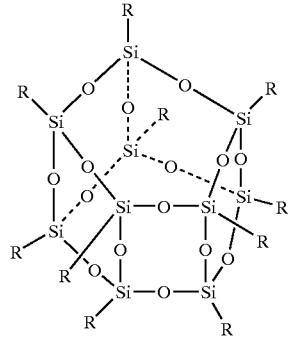

$[(RSiO_{1.5})_{10}]\Sigma 10$

Formula 3

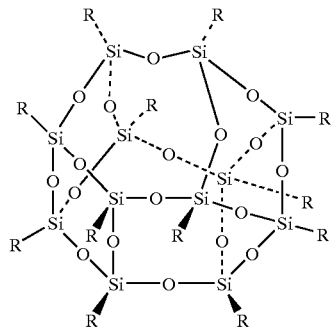

$[(RSiO_{1.5})_{12}]\Sigma 12$

Formula 4

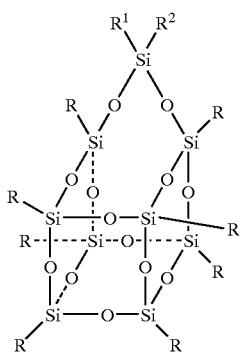

Formula 5

[(RSiO$_{1.5}$)$_8$(R$^1$R$^2$SiO$_{1.0}$)$_1$]Σ9

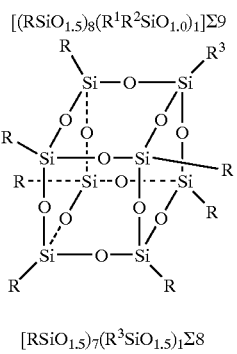

Formula 6

[RSiO$_{1.5}$)$_7$(R$^3$SiO$_{1.5}$)$_1$Σ8

SECTION A

Manipulations of Silicon-oxygen Frameworks in POSS Systems

The invention provides for manipulation of silicon-oxygen frameworks in POSS Systems. Such processes utilize acid reagents and POSS compounds[(RSiO$_{1.5}$)$_n$]$_{\Sigma\#}$, where R=organic substituent (H. cyclic or linear aliphatic, aromatic, olefinic, alkoxy or siloxy groups that can additionally contain reactive functionalities such as alcohols, esters, amines, ketones, olefins and ethers) and where n=an integer from 4 to 14 with n=6–12 being preferred. The processes allow for the conversion of low cost, easily produced polyhedral oligomeric silsesquioxanes of the formula [(RSiO$_{1.5}$)$_n$]$_{\Sigma\#}$ to be converted into more desirable polyhedral oligomeric silsesquioxanes of the type [(RSiO$_{1.5}$)$_m$(RXSiO$_{1.0}$)$_n$]$_{\Sigma\#}$ where m=1–12, n=4–24 and X=the weak conjugate base of the strong acid including F, OH, SH, NHR or NR2 (where R=as defined above), ClO$_4$, SO$_4$, SO$_3$CF$_3$, SO$_3$Cl, SO$_3$CH$_3$, NO$_3$, PO$_4$, Cl or OH. Formulations of the type [(RSiO$_{1.5}$)$_m$(RXSiO$_{1.0}$)$_n$]$_{\Sigma\#}$ can be used as stand-alone chemical reagents or further derivatized into a diverse number of other POSS chemical species.

Thus polyhedral oligomeric silsesquioxanes of the type [(RSiO$_{1.5}$)$_6$]$_{\Sigma 6}$ (Formula 1) are readily converted using the above mentioned acids into formula [(RSiO$_{1.5}$)$_4$(RXSiO$_{1.0}$)$_2$]$_{\Sigma 6}$, Formula 7 and [(RSiO$_{1.5}$)$_2$(RXSiO$_{1.0}$)$_4$]$_{\Sigma 6}$, where Formula 8 and Formula 9 are geometrical isomers. Also a twisted cage can be formed per formula 7d.

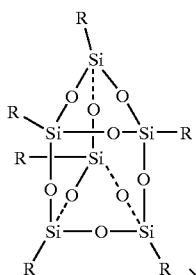

Formula 1

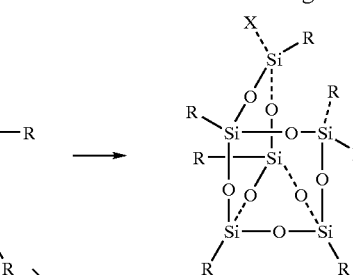

Formula 7a

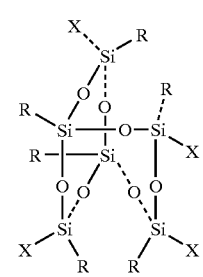

Formula 8a

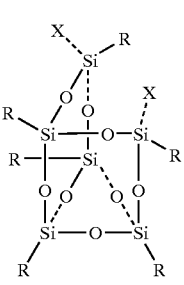

Formula 7c

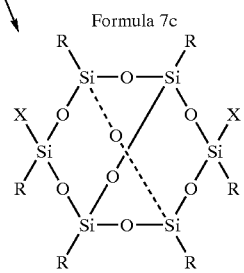

Formula 9a

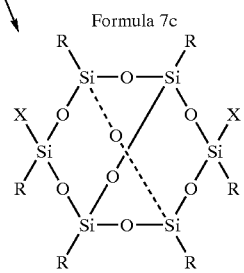

Formula 7d

Also polyhedral oligomeric silsesquioxanes of the type $[(RSiO_{1.5})_8]_{\Sigma 8}$ (Formula 2) are readily converted using the above mentioned acids into formula $[(RSiO_{1.5})_6(RXSiO_{1.0})_2]_{\Sigma 8}$, where Formula 10 and Formula 11 are geometrical isomers.

Polyhedral oligomeric silsesquioxanes of the type $[(RSiO_{1.5})_m(R^3SiO_{1.5})_n]_{\Sigma\#}$ [such as $[(RSiO_{1.5})_7(R^3SiO_{1.5})_1]_{\Sigma 8}$, Formula 6], where more than one type of R is contained within the same molecule and are readily converted, using the above mentioned acids, into a variety of isomers of formula $[(RSiO_{1.5})_6(RXSiO_{1.0})_1(R^3XSiO_{1.0})_1]_{\Sigma 8}$, where Formula 12a, Formula 12b, and Formula 12c are all geometrical isomers.

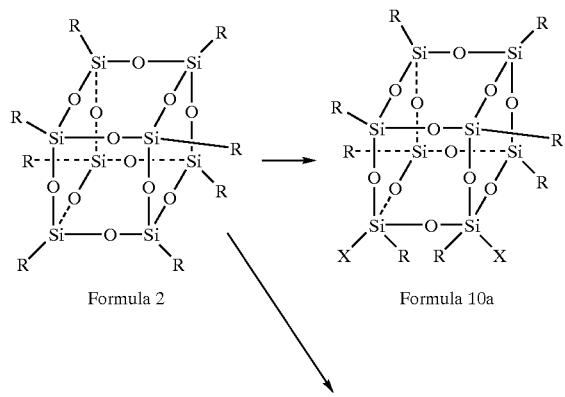

Formula 2    Formula 10a

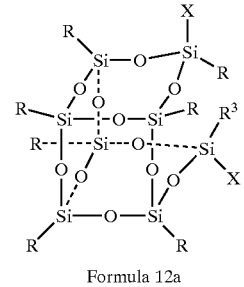

Formula 12a

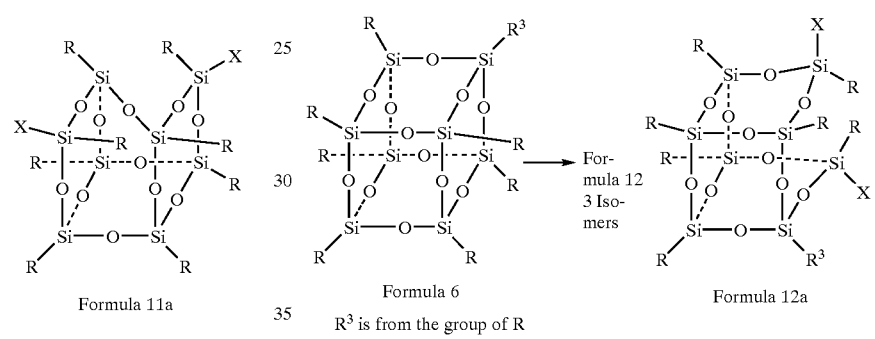

Formula 11a    Formula 6    Formula 12a $R^3$ is from the group of R but different than R in this case → Formula 12 3 Isomers Thus the present invention also provides processes that promote the structural rearrangement of silicon-oxygen frameworks, e.g., the conversion of Formula 1 to Formula 7d and of Formula 2 to Formula 11.

It is desirable to rearrange the silicon-oxygen frameworks in POSS systems in order to change the overall 3-dimensional topology of POSS molecules and thereby tailor their physical properties. Through rearranging the silicon-oxygen structural frameworks, improvements in mechanical properties such as tensile, compressive, abrasion resistance, modulus and thermal properties such as glass and melt transition temperatures as well as morphological and microstructural control can be better achieved in polymer systems which contain POSS.

The structural rearrangement of POSS's silicon-oxygen frameworks involves the following sequence: opening of the silicon oxygen ring, rearrangement of the framework, closure of the framework. The processes in this disclosure describe the use of acidic reagents to open POSS's silicon-oxygen rings and in some cases these same processes and conditions also promote the rearrangement of the rings. The closure of the rings usually involve the net elimination of at least one or more oxygen atoms from silicon-oxygen framework as compared to the original formula. For example, the conversion of formula 1 to formula 7d (or formula 2 into formula 11) necessarily involves the elimination of an oxygen atom from the framework. The oxygen atom that has been removed from the framework may either be eliminated entirely from the POSS molecule or it may be relocated external to the framework as a reactive functionality such as a silanol.

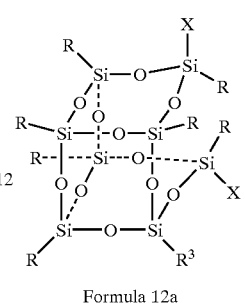

Formula 12a

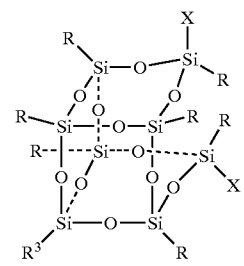

Formula 12a

The action of the above mentioned acids and reagents can also be controlled in such a manner that the silicon atoms can be entirely removed from the silicon oxygen frameworks of polyhedral oligomeric silsesquioxanes. The process is especially effective when silsesquioxanes of the formula $[(RSiO_{1.5})_m(R^3SiO_{1.5})_n]_{\Sigma\#}$ [such as $[(RSiO_{1.5})_7(R^3SiO_{1.5})_1]_{\Sigma 8}$), Formula 6], which contain more than one type of R group, are utilized. In such cases formula of the type $[(RSiO_{1.5})_4(R^3XSiO_{1.0})_3]_{\Sigma 7}$ can be prepared. This represents an entirely new synthetic route for the preparation of the very useful incompletely condensed trisilanol reagents such as $[(RSiO_{1.5})_4(R^3XSiO_{1.0})_3]_{\Sigma 7}$ where X=OH in particular. Formulas 13a and 13b are stereochemical isomers.

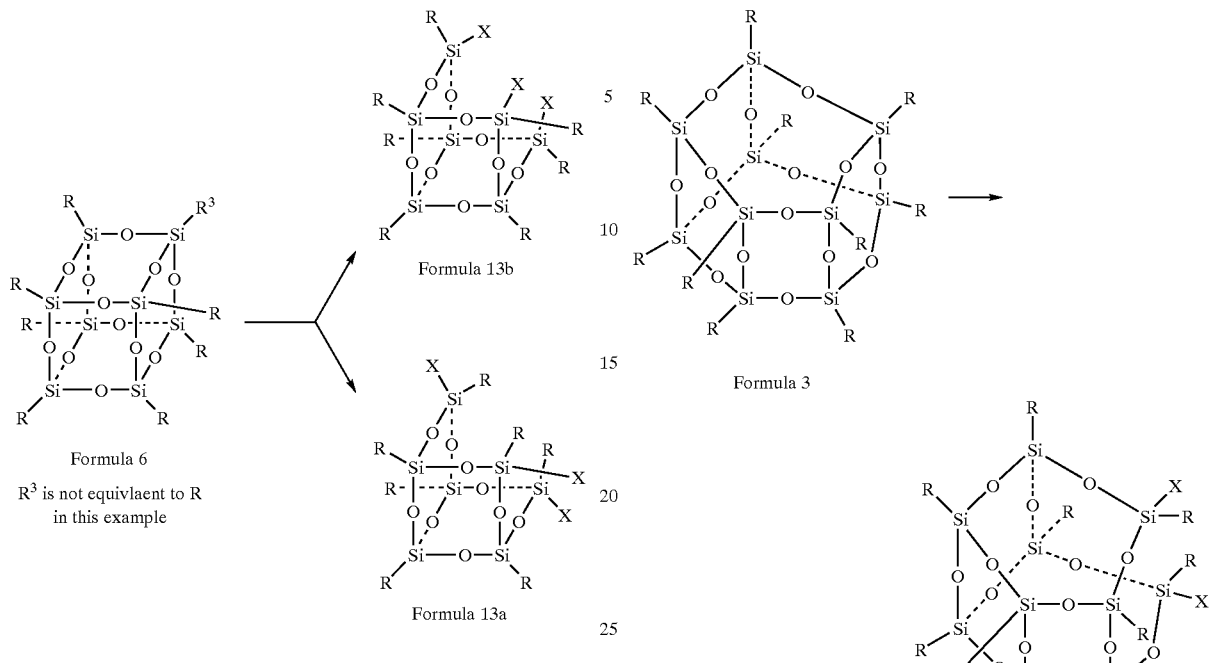
Polyhedral oligomeric silsesquioxanes of the type $[(RSiO_{1.5})_{10}]_{\Sigma 10}$ (Formula 3) and $[(RSiO_{1.5})_{12}]_{\Sigma 12}$ (Formula 4) are also readily converted using the above mentioned acids into formula $[(RSiO\ 1.5)_8(RXSiO_{1.0})_2]_{\Sigma 10}$ (Formula 14a) or $[(RSiO_{1.5})_{10}(RXSiO_{1.0})_2]_{\Sigma 12}$ where Formula 15a and Formula 15b are geometrical isomers.
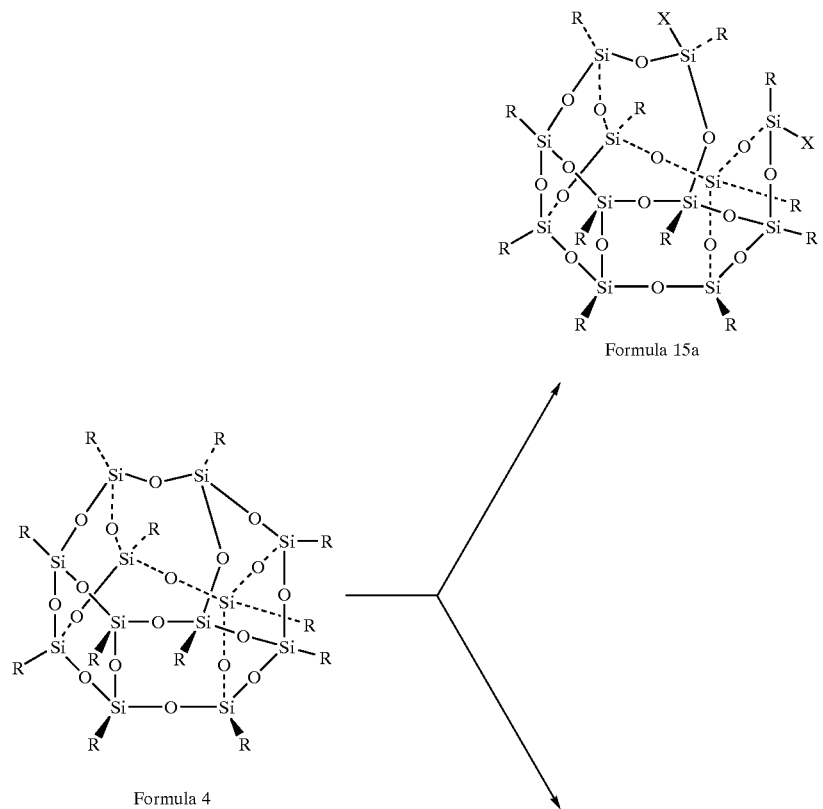

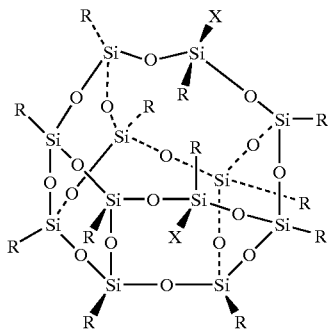

Formula 15b

Process Variables Controlling the Manipulation of POSS Frameworks

As is typical with chemical processes there are a number of variables that can be used to control the purity, selectivity, rate and mechanism of any process. Variables influencing the process for the cleavage and manipulation of silicon-oxygen frameworks in polyhedral oligomenic silsesquioxanes include the following: chemical class of acid, silicon-oxygen ring size, silicon-oxygen ring type $[(RSiO_{1.5})_m]_{\Sigma \geq 190}$, (silsesquloxane), $[(RSiO_{1.5})_m(RSiO_{1.0})_n(R_2Si)_j]_{\Sigma\#}$ (silsesquioxane-siloxane), $[(RSiO_{1.5})_m(RSiO_{1.0})_n(ROSi)_j]_{\Sigma\#}$ (silsesquioxane-silicate), (where m=1–12 and n=4–24, j=1–8), effect of the organic substituents, process temperature, process solvent, process catalyst. Each of these variables is briefly discussed below. It is also envisioned that specific catalysts can be developed to promote or enhance the cage-opening action of the acids. Specifically, Lewis acids, including zinc compounds (e.g. $ZnBr_2$, $ZnCl_2$ and $ZnF_2$ as well as $SnCl_4$, $SbCl_5$, $FeCl_3$ and $TiCl_4$) aluminum compounds (e.g. $Al_2H_6$, $LiAlH_4$, $AlI_3$, $AlBr_3$, $AlCl_3$ and $AlF_3$) boron compounds (e.g. $RB(OH)_2$, $BI_3$, $BBr_3$, $BCl_3$ and $BF_3$) are known to play important roles in the ring-opening polymerization of cyclic silicones in the ring-opening of polyhedral oligomeric silsesquioxanes.

Chemical Class of Acids

There are a number of strong acids that can be used to open the silicon-oxygen framework in POSS compounds. We have found that the acids such as $HBF_4$ operating in the presence of $BF_3$ are highly effective for cage-opening reactions. This acid is particularly effective for producing cage-opened products with exo-functionalities such as Formula 7–15 The effective ratio of $HBF_4/BF_3$ ranges from 0.25 to 10 with a ratio of 2.5 being preferred. The concentration of $HBF_4/BF_3$ can be varied and impacts both the extent and selectivity of the process. For example a deficiency of $HBF_4/BF_3$ to POSS is used to produce an POSS-exodifluoride product Formula 7 that has been side opened. The use of an excess of $HBF_4/BF_3$ to POSS, results in POSS-exotetrafluoride products Formula 8 and Formula 9 that have undergone two or more cage openings. Selectivity to produce singly cage-opened products can be carried out using a deficiency of $HBF_4/BF_3$ to POSS reagent in a 1.0 molar equivalents of $HBF_4$ to 3.0 molar equivalents of $BF_3$ ratio with a ratio of 1.5 being preferred. The $HBF_4/BF_3$ combination is effective at opening the silicon-oxygen frameworks at 24° C. and 1 atmosphere, however it is recognized that variations in temperature and pressure can be used to either enhance or reduce the action of this system. It is also recognized that the use of other co-reagents such as $BCl_3$, boron oxides, aluminum oxides, zinc oxides may be used in place of $BF_3$ to promote the cage opening process through dehydration or other means.

Alternatively other strong acids and mixtures of strong acids can be utilized to carryout the cage-opening reactions. Classes of these acids include: sulfonic acids (e.g. $HSO_3CF_3$ triflic acid, $HSO_3Cl$ chlorosulfonic acid, $HSO_3CH_3$ methanesulfonic acid, and toluenesulfonic acids e.g. tosylates), superacids (e.g. $HF/SbF_5$), mineral acids (e.g. HI, HBr, HCl, $H_2SO_4$, $HNO_3$, $HClO_4$). In some cases the anhydride of these acids may also be utilized provided that there is a trace amount of water present to generate a catalytic amount of the acid from the anhydride. This is particularly the case with triflic anhydride which is the anhydride of triflic acid. One advantage of using the anhydride over the acid is that the anhydride may facilitate the reaction by acting both as an acid source and as a dehydrating agent. This eliminates the need for co-reagents such as $BF_3$ mentioned above.

There are additional advantages of using the above listed acids over the $HBF_4/BF_3$ system in terms of controlling the stereochemistry of the cage-opened product and the extent of reaction. For example triflic acid (and triflic anhydride) is effective at opening POSS compounds to form exo-$[(RSiO_{1.5})_m(R(F_3CSO_3)SiO_{1.0})_n]_{\Sigma\#}$ complexes that upon undergoing hydrolysis can be used to produce POSS systems with endo stereochemistry (e.g. endo-$[(RSiO_{1.5})_m(R(HO)SiO_{1.0})_n]_{\Sigma\#}$ compounds). When triflic acid or methanesulfonic acids are employed for the manipulation of the silicon oxygen frameworks in POSS cages, a 2–12 fold excess of the acid, relative to the molar equivalence of POSS, is suitable, with a 6 fold excess being preferred.

Silicon-oxygen Ring Size, Ring Type and Cage Sizes

The process discussed in this disclosure is not limited to specific sizes of POSS cages. As shown the process can be carried out on cages containing four to fourteen or more silicon atoms making up the silicon-oxygen framework. It has been noted that the silicon-oxygen ring size contained within such POSS systems does affect the rate at which cage opening can occur. For example rings containing three silicon atoms and three oxygen atoms as in Formula 1, appear to open faster than the larger rings containing 4 silicons and 4 oxygens (Formula 2). The relative rate for the opening of POSS silicon-oxygen rings appears to be six membered rings with three silicons>eight membered rings with four silicons>ten membered rings with five silicons>twelve membered rings with six silicons. Knowledge of this information allows the user of this process to control which silicon-oxygen rings within a POSS molecule will be opened. For example Formula 1 contains two six-membered rings and three eight membered silicon oxygen rings yet because the six membered rings within the molecule open at a faster rate than the eight membered rings, the molecule can be selectively functionalized at sites along the six membered ring to form Formula 7 and Formula 8.

and nonhalogenated). The variables of solvent type, POSS concentration, and process temperature should be utilized in the standard way to match the specific cage opening process to the equipment available Table of Selected POSS Feedstocks and their Cage-opened Products.

| Starting POSS | Acid Reagents | Yield (%) | New POSS System |
|---|---|---|---|
| $[(c\text{-}C_6H_{11}SiO_{1.5})n]_{\Sigma 6}$ | $HBF_4/BF_3$ | 13.6 | $[(c\text{-}C_6H_{11}SiO_{1.5})_2(c\text{-}C_6H_{11}(F)SiO_{1.0})_4]_{\Sigma 6}$ (Formula 8, X = F) |
| | | 0.2 | $[(c\text{-}C_6H_{11}SiO_{1.5})_2(c\text{-}C_6H_{11}(F)SiO_{1.0})_4]_{\Sigma 6}$ (Formula 9, X = F) |
| | | 68 | $[(c\text{-}C_6H_{11}SiO_{1.5})_4(c\text{-}C_6H_{11}(F)SiO_{1.0})_2]_{\Sigma 6}$ (Formula 7a, X = F) |
| | | 10.2 | $[(c\text{-}C_6H_{11}SiO_{1.5})_2(c\text{-}C_6H_{11}(F)SiO_{1.0})_1(c\text{-}C_6H_{11}(HO)SiO_{1.0})_1]_{\Sigma 6}$ (Formula 7c, X = OH, F) |
| $[(c\text{-}C_6H_{11}SiO_{1.5})_6]_{\Sigma 6}$ | $HBF_4/BF_3$ | 92 | $[(c\text{-}C_6H_{11}SiO_{1.5})_2(c\text{-}C_6H_{11}(F)SiO_{1.0})_4]_{\Sigma 6}$ (Formula 8, X = F) |
| | | 8 | $[(c\text{-}C_6H_{11}SiO_{1.5})_2(c\text{-}C_6H_{11}(F)SiO_{1.0})_4]_{\Sigma 6}$ (Formula 9, X = F) |
| $[(c\text{-}C_6H_{11}SiO_{1.5})_6]_{\Sigma 6}$ | MsOH | 70 | $[(c\text{-}C_6H_{11}SiO_{1.5})_4(c\text{-}C_6H_{11}(MS)SiO_{1.0})_2]_{\Sigma 6}$ (Formula 7d, X = OMs) |
| $[(H_2C=CHSiO_{1.5})_8]_{\Sigma 8}$ | $HBF_4/BF_3$ | 37 | $[(H_2C=CHSiO_{1.5})_6(H_2C=CH(F)SiO_{1.0})_2]_{\Sigma 8}$ (Formula 10, X = F) |
| $[(C_2H_5SiO_{1.5})_8]_{\Sigma 8}$ | $HBF_4/BF_3$ | 80 | $[(C_2H_5SiO_{1.5})_6(C_2H_5(F)SiO_{1.0})_2]_{\Sigma 8}$ (Formula 10, X = F) |
| $[(C_2H_5SiO_{1.5})_8]_{\Sigma 8}$ | $H_2SO_4/SO_3$ | 7 | $[(C_2H_5SiO_{1.5})_6(C_2H_5(HO_3SO)SiO_{1.0})_2]_{\Sigma 8}$ (Formula 10, X = $OSO_3H$) |
| | | 21 | $[(C_2H_5SiO_{1.5})_6(C_2H_5(HO_3SO)SiO_{1.0})_2]_{\Sigma 8}$ (Formula 11, X = $OSO_3H$) |
| $[(C_2H_5SiO_{1.5})_8]_{\Sigma 8}$ | $ClSO_3H$ | 31 | $[(C_2H_5SiO_{1.5})_6(C_2H_5(ClO_2SO)SiO_{1.0})_2]_{\Sigma 8}$ (Formula 10, X = $OSO_2Cl$) |
| $[(c\text{-}C_6H_{11}SiO_{1.5})_8]_{\Sigma 8}$ | $HBF_4/BF_3$ | 85 | $[(c\text{-}C_6H_{11}SiO_{1.5})_6(c\text{-}C_6H_{11}(F)SiO_{1.0})_2]_{\Sigma 8}$ (Formula 10, X = F) |
| $[(c\text{-}C_6H_{11}SiO_{1.5})_8]_{\Sigma 8}$ | TfOH | 100 | $[(c\text{-}C_6H_{11}SiO_{1.5})_6(c\text{-}C_6H_{11}(TfO)SiO_{1.0})_2]_{\Sigma 8}$ (Formula 10, X = OTf) |
| $[(c\text{-}C_6H_{11}SiO_{1.5})_8]_{\Sigma 8}$ | $Tf_2O$ | 100 | $[(c\text{-}C_6H_{11}SiO_{1.5})_6(c\text{-}C_6H_{11}(TfO)SiO_{1.0})_2]_{\Sigma 8}$ (Formula 10, X = OTf) |
| $[(c\text{-}C_6H_{11}SiO_{1.5})_8]_{\Sigma 8}$ | TfOH | 70 | $[(c\text{-}C_6H_{11}SiO_{1.5})_6(c\text{-}C_6H_{11}(TfO)SiO_{1.0})_2]_{\Sigma 8}$ (Formula 11, X = OTf) |
| $[(p\text{-}CH_3C_6H_4SiO_{1.5})_8]_{\Sigma 8}$ | $HBF_4/BF_3$ | 80 | $[(p\text{-}CH_3C_6H_4SiO_{1.5})_6(p\text{-}CH_3C_6H_4(F)SiO_{1.0})_2]_{\Sigma 8}$ (Formula 10, X = F) |
| $[(c\text{-}C_6H_{11}SiO_{1.5})_7(C_6H_5CH_2SiO_{1.5})_1]_{\Sigma 8}$ | $HBF_4/BF_3$ | 66 | $[(c\text{-}C_6H_{11}SiO_{1.5})_6(c\text{-}C_6H_{11}(F)SiO_{1.0})_1(C_6H_5CH_2(F)SiO_{1.0})_1]_{\Sigma 8}$ (Formula 10, X = F) |
| $[(c\text{-}C_5H_9SiO_{1.5})_7(CH_3SiO_{1.5})_1]_{\Sigma 8}$ | $HBF_4/BF_3$ | 33 | $[(c\text{-}C_5H_9SiO_{1.5})_6(c\text{-}C_5H_9(F)SiO_{1.0})_1(CH_3(F)SiO_{1.0})_1]_{\Sigma 8}$ (Formula 10, X = F) |
| $[(CH_3SiO_{1.5})_{10}]_{\Sigma 10}$ | $HBF_4/BF_3$ | 24 | $[(CH_3SiO_{1.5})_8(CH_3(F)SiO_{1.0})_2]_{\Sigma 10}$ (Formula 14, X = F) |
| $[(c\text{-}C_6H_{11}SiO_{1.5})_{12}]_{\Sigma 12}$ | $HBF_4/BF_3$ | 70 | $[(c\text{-}C_6H_{11}SiO_{1.5})_{10}(c\text{-}C_6H_{11}(F)SiO_{1.0})_2]_{\Sigma 12}$ (Formulas 15a and 15b, X = F) $[(c\text{-}C_6H_{11}SiO_{1.5})_8(c\text{-}C_6H_{11}(F)SiO_{1.0})_4]_{\Sigma 12}$ |

(a) TfOH = $CF_3SO_3H$; MsOH = $CH_3SO_3H$; $H_2SO_4/SO_3$ = 20% fuming sulfuric acid Effect of the Organic Substituent, Process Solvents and Process Temperatures The process described in this disclosure is not limited to POSS systems bearing specific organic groups (defined as R) attached to the silicon atom of the silicon-oxygen ring systems. The processes are amenable to opening the POSS systems bearing a wide variety of organic groups. The organic substituent does have a large effect on the solubility of both the final product and the starting POSS material. Therefore it is envisioned that the different solubilities between the starting POSS compounds and their respective cage-opened products can be used to facilitate the separation of and purification of the final reaction products. The process has been carried out in a wide range of solvents such as $CCl_4$, $CHCl_3$, $CH_2Cl_2$, fluorinated solvents, aromatics (halogenated and nonhalogenated), aliphatic (halogenated

SECTION B

Isomers of POSS Systems

Given the three dimensional and nanoscopic nature of POSS systems it is important to realize that a number of isomeric forms for any given formula can be produced by the methods of the invention. The stereochemistry of these isomers can be controlled by the inventive methods taught herein, however, in some cases geometrical isomers will still exist. A number of examples are provided to convey the presence of such isomers and that the invention is not limited to those stereochemical or geometrical isomers shown herein.

Examples of six isomers for difunctional incompletely condensed $[(RSiO_{1.5})_4(RXSiO_{1.0})_2]_{\Sigma 6}$ systems are:

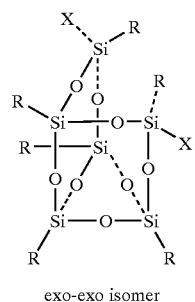

Formula 7a exo-exo isomer

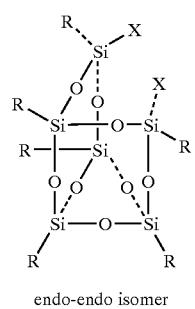

Formula 7b endo-endo isomer

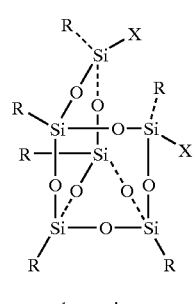

Formula 7c endo-exo isomer

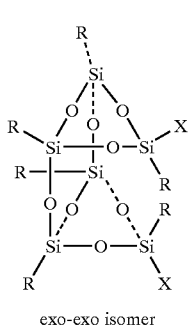

Formula 16a exo-exo isomer

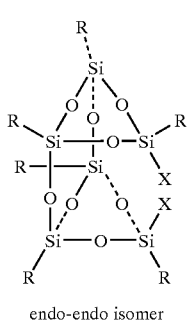

Formula 16b endo-endo isomer

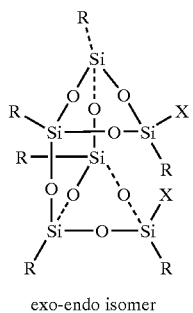

Formula 16c exo-endo isomer

Note that Formula 7 differs from formula 16 in that the silicon-oxygen framework of formula 7 has been cleaved along one of its six membered rings while formula 16 has been cleaved along one of its eight membered rings.

Examples of eight isomers for tetrafunctional twisted $[(RSiO_{1.5})_2(RSiO_{1.0})_4]_{\Sigma 6}$ systems are:

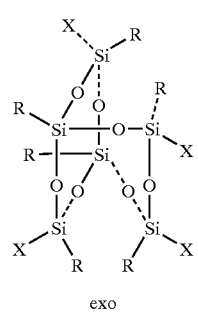

Formula 8a exo

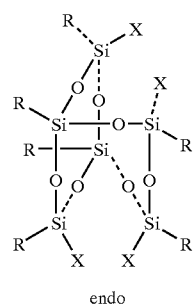

Formula 8b endo

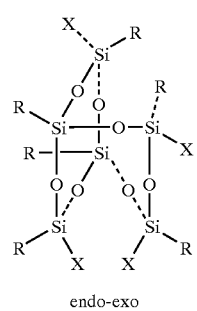

Formula 8c endo-exo

Formula 8d
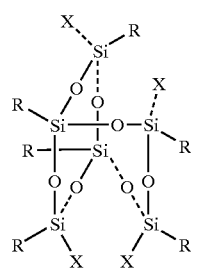
endo-exo mixed
Formula 8e
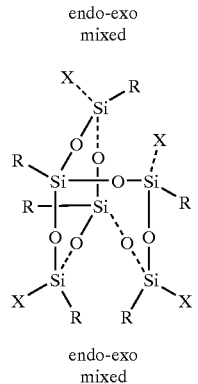
endo-exo mixed
Formula 8f
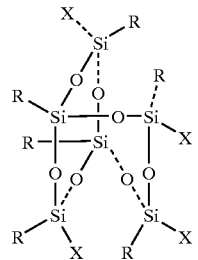
endo-exo mixed
Formula 8g
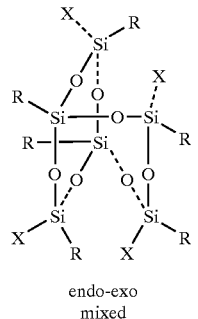
endo-exo mixed
Formula 8h
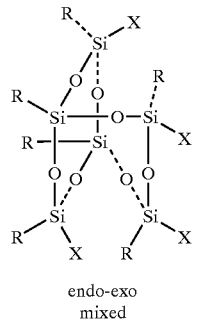
endo-exo mixed
Examples of six isomers for tetrafunctional incompletely condensed $[(RSiO_{1.5})_2(RXSiO_{1.0})_4]_{\Sigma 6}$ systems are:
Formula 9a
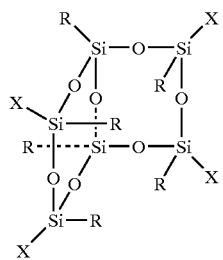
exo
Formula 9b
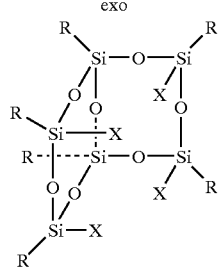
endo
Formula 9c
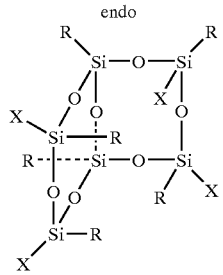
endo-exo mixed
Formula 9d
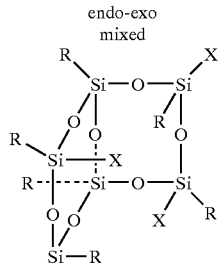
endo-exo
Formula 9e
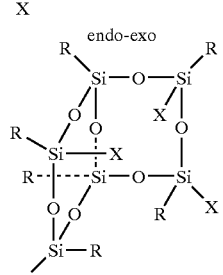
endo-exo
Formula 9f
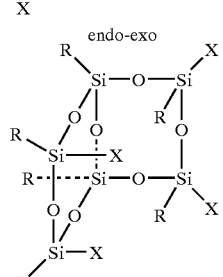
endo-exo Examples of three isomers for difunctional twisted $[(RSiO_{1.5})_6(RXSiO_{1.0})_2]_{\Sigma 8}$ systems are:

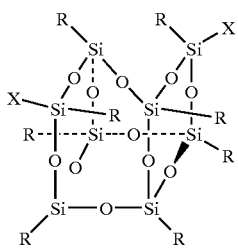

Formula 11a

Exo

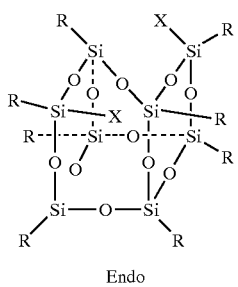

Formula 11b

Endo

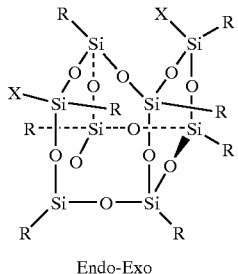

Formula 11c

Endo-Exo

Examples of twelve isomers for difunctional $[(RSiO_{1.5})_6(R^3XSiO_{1.0})_1(RXSiO_{1.0})_1]_{\Sigma 8}$ systems are:

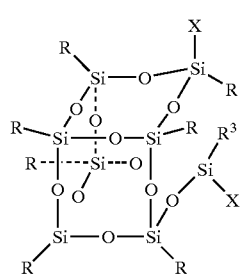

exo-formula 12a–d 4 isomers total
1 exo
1 endo
2 endo-exo

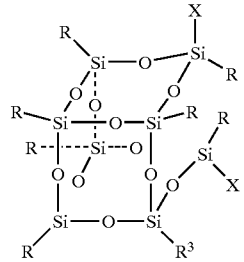

exo-formula 12e–h 4 isomers total
1 exo
1 endo
2 endo-exo

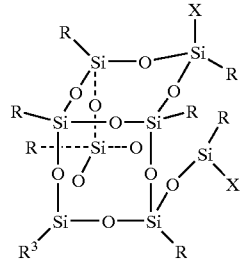

exo-formula 12i–l 4 isomers total
1 exo
1 endo
2 endo-exo

SECTION C
Methods for Controlling Stereochemistry

The processes described above enable the manipulation of the silicon-oxygen frameworks within any POSS molecular structure. However it is advantageous to control the stereochemistry of the reactive functionalities now located on these molecules. Four general processes have now been identified to accomplish any type of stereochemical manipulation that is so desired. It is important to note that POSS molecules are three-dimensional nanostructured molecular systems and because of this the primary stereochemical considerations are whether the functionality in question is oriented externally or internally with respect to the center of a particular face (or side) of the cage. If a functionality is projected externally (away from) the center face of the cage it is referred to as having exo-stereochemistry while functionalities projecting toward the center of any face are referred to as having endo stereochemistry. Depending on the type of manipulation or desired use for the cage, it is of high value to the material manufacturer (chemist) to control the stereochemical nature of such products. Again these techniques can be used to control the stereochemistry of X functionalities on any size of POSS cage.

Method 1
Process for the Inversion of Stereochemistry

This method involves the hydrolysis of the X group on formulas 7, 10 to a silanol species of formulas 7, 10 with inversion of stereochemistry. The method is particularly useful for all X groups excluding fluoride. The method can also be utilized to alter the stereochemistry of silanol functionalized versions of formula 7, 10 and simply involves treatment of the silanol with $HBF_4$ to form the intermediate species containing the conjugate base of the acid. Treatment of this species with acidic water reproduces the silanol species with inverted stereochemistry. The process can be used to convert both endo and exo stereochemical orientation of groups. The process is applicable to any size of POSS cage where n=4 to 14 in $[(RSiO_{1.5})_n]_{\Sigma \#}$.

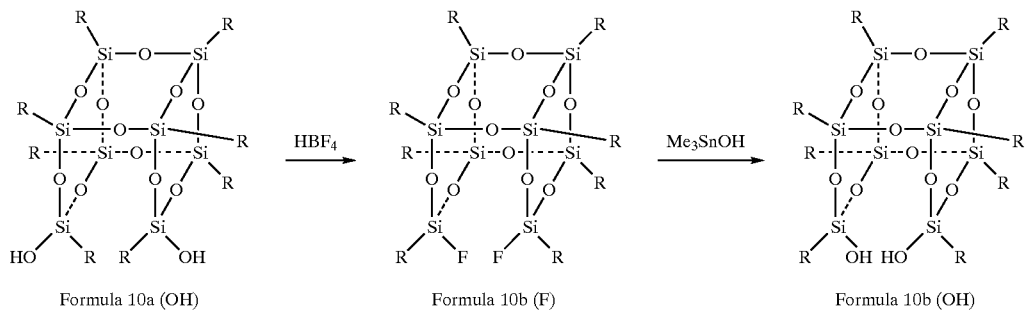

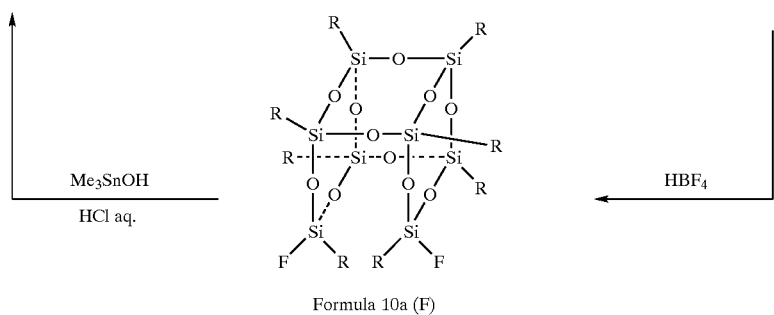

Method 1 can be used to alter the stereochemistry of X groups on all sizes of polyhedral oligomeric silsesquioxane cages. The example below shows that the process can be carried out on POSS systems bearing six silicon atoms within the framework.

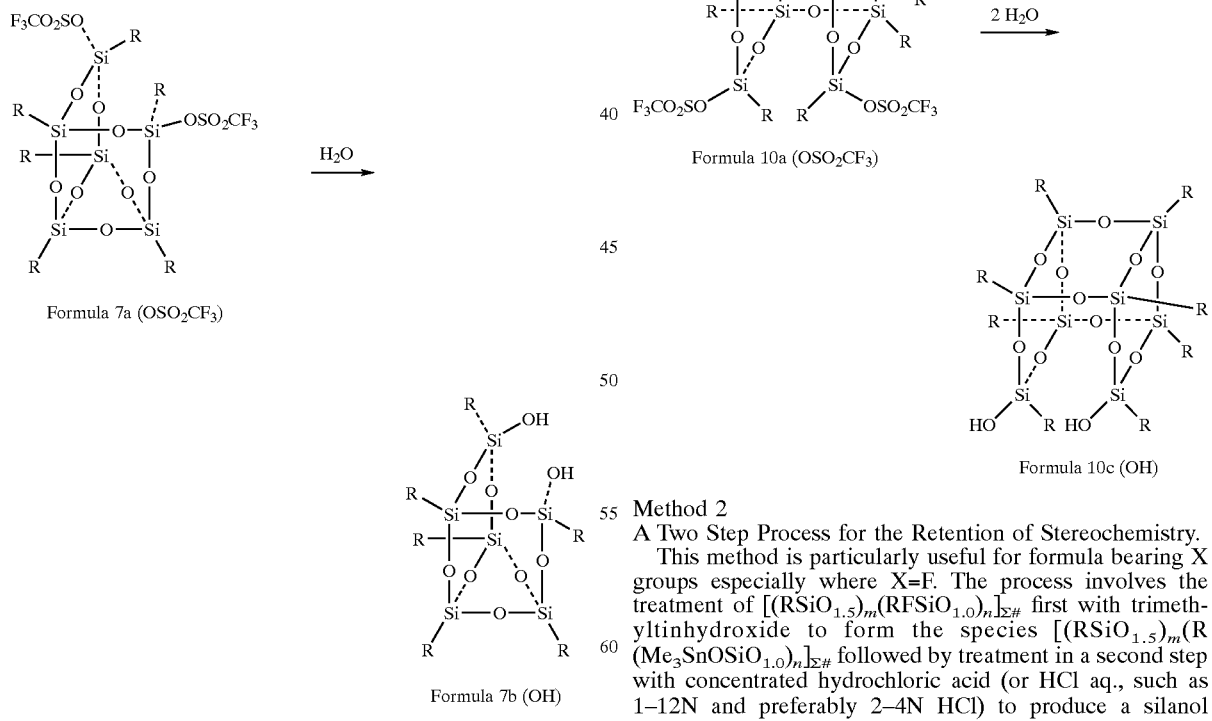

In some instances it is possible to carry out the conversion process so formula-bearing mixed stereochemical (endo-exo) functionalities are formed.

Method 2
A Two Step Process for the Retention of Stereochemistry.

This method is particularly useful for formula bearing X groups especially where X=F. The process involves the treatment of $[(RSiO_{1.5})_m(RFSiO_{1.0})_n]_{\Sigma\#}$ first with trimethyltinhydroxide to form the species $[(RSiO_{1.5})_m(R(Me_3SnOSiO_{1.0})_n]_{\Sigma\#}$ followed by treatment in a second step with concentrated hydrochloric acid (or HCl aq., such as 1–12N and preferably 2–4N HCl) to produce a silanol species $[(RSiO_{1.5})_m(R(HO)SiO_{1.0})_n]_{\Sigma\#}$ in which the silanol groups occupy the same stereochemical position relative to the F groups in the starting compound. The process is applicable to any size of POSS cage where n=4 to 14 in $[(RSiO_{1.5})_n]_{\Sigma\#}$.

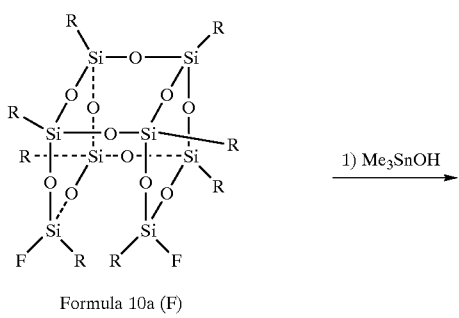

Formula 10a (F)

1) Me₃SnOH

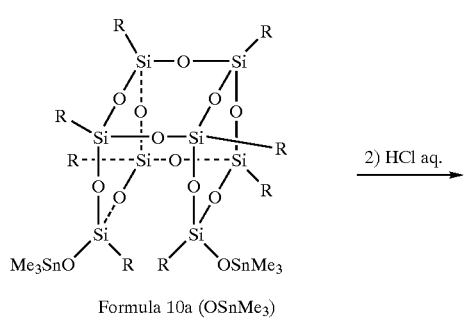

Formula 10a (OSnMe₃)

2) HCl aq.

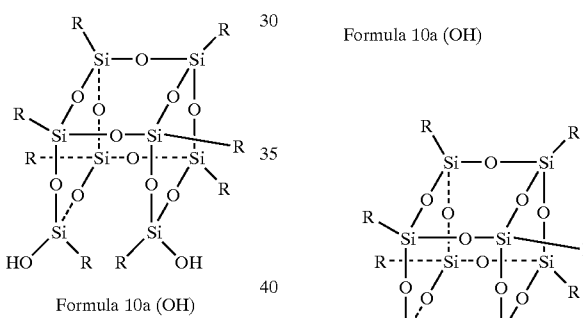

Formula 10a (OH)

Reactions of Formula 7a or 10a with Grignard reagents (RMgX) or hydride reducing agents (such as LiAlH₄ and Al₂H₆) also proceed with inversion of stereochemistry to produce the corresponding di-exo species of Formulas 7a and 10a.

Method 2 can be used to alter the stereochemistry of X groups on all sizes of polyhedral oligomeric silsesquioxane cages. The example below shows that the process can be carried out on POSS systems bearing six silicon atoms within the framework.

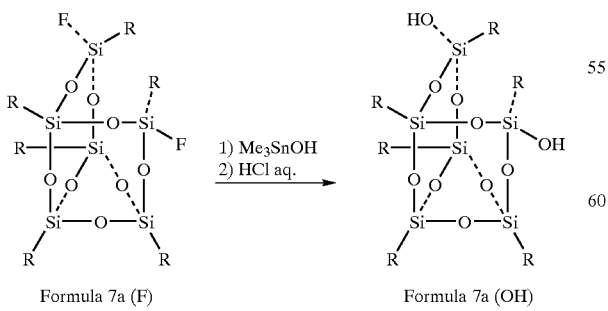

Formula 7a (F)    1) Me₃SnOH    Formula 7a (OH)
                  2) HCl aq.

Reactions of Formula 7a or 10a with alkyllithium reagents (e.g., CH₃Li, C₆H₅CCLi and CH₂=CHLi) also proceed with retention of stereochemistry to produce the corresponding di-exo species of Formulas 7a and 10a.

Method 3

A Three Step Process for Inversion of Stereochemistry

A variation of the Method 2 process can be utilized to invert the stereochemistry of silanol groups. The method provides treatment of the silanol species $[(RSiO_{1.5})_m(R(HO)SiO_{1.0})_n]_{\Sigma\#}$ with $HBF_4/BF_3$ to produce the $[(RSiO_{1.5})_m(R(F)SiO_{1.0})_n]_{\Sigma\#}$ species followed by subsequent treatment with Me₃SnOH and concentrated HCl as described above. The process is applicable to any size of POSS cage where n=4 to 14 in $[(RSiO_{1.5})_n]_{\Sigma\#}$.

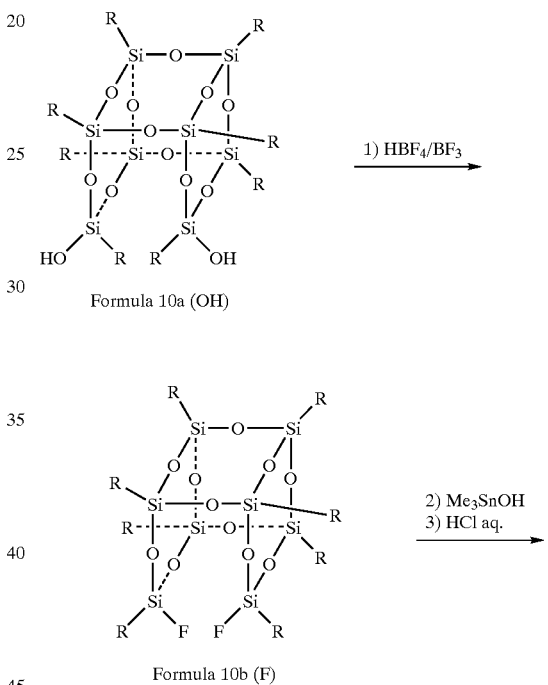

Formula 10a (OH)

1) HBF₄/BF₃

Formula 10b (F)

2) Me₃SnOH
3) HCl aq.

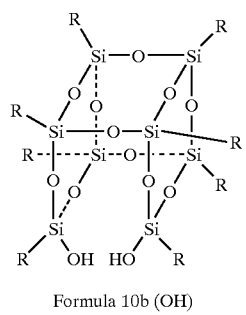

Formula 10b (OH)

Method 3 can be used to invert the stereochemistry of X groups on all sizes of polyhedral oligomeric silsesquioxane cages. The example below shows that the process can be carried out on POSS systems bearing six silicon atoms within the framework.

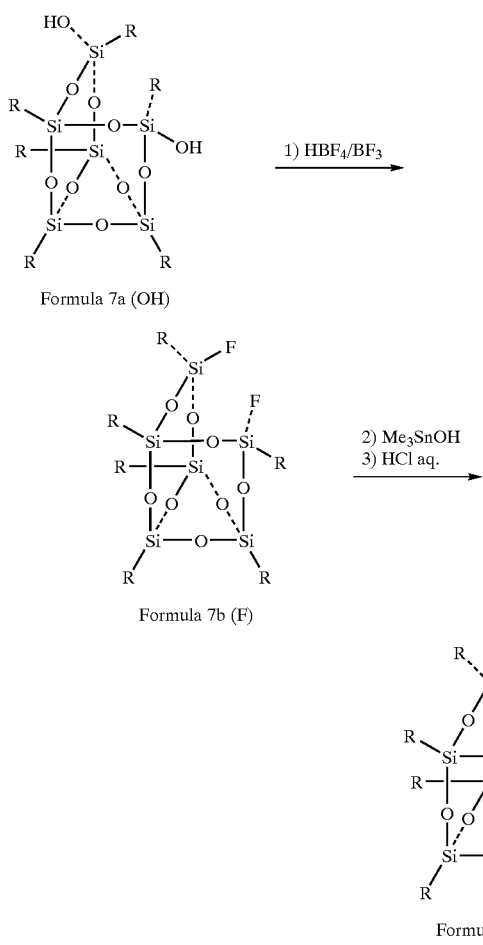

SECTION D

POSS Cage Expansions and New Reagent Synthesis

This section shows that the incompletely condensed POSS-silanols are very valuable reagents as they can be used to produce even more diverse POSS feedstocks. Examples are listed for expansion of formula 7, 8, 10. Note that in such processes formula bearing silanol groups with endo-stereochemistry are particularly useful for reacting with $Y_2SiR^1R^2$ silane reagents where $R^1$ and $R^2$ are the same or different from the group previously defined for R (e.g. $R^1$=H, methyl, ethyl, vinyl, allyl and phenyl) while Y=halides (e.g. Cl, Br, I) or amines such as $NR_2$ (e.g. dimethylamine $N(CH_3)_2$, $N(CH_2CH_3)_2$, etc.). The process of reacting formula 7 or formula 8 with either one or two equivalents of $Y_2SiR^1R^2$ silane reagents results in a net expansion of the number of silicon atoms contained within the silicon oxygen framework of the original formula. In this manner the silicon-oxygen framework structures can be selectively enlarged as well as functionalized. This process is important because Formula 5 has undergone a formal expansion of the number of silicon atoms contained within its ring systems. Such an expansion is unprecedented and the rings now contain both $(RSiO_{1.5})$ and $(R_2SiO)$ types of silicon atoms. Furthermore, functionalities useful for polymerizations and grafting can be incorporated into the molecule through the two organic R-groups located on the $R_2SiO$ silicon atom.

Method 4
Combination of the Above Methods for Full Manipulation of X Groups and Stereochemistry.

The methods described for controlling the stereochemistry in these systems can also be effectively used in tandem to both vary the chemical nature of the X group in $[(RSiO_{1.5})_m(RXSiO_{1.0})_n]_{\Sigma\#}$ systems as well as to interconvert the stereochemical nature of the X groups. Therefore any and all stereochemical isomers for the formulas described in this work are accessible and to be claimed.

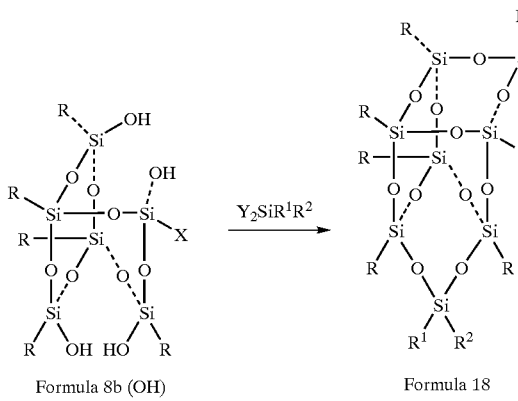

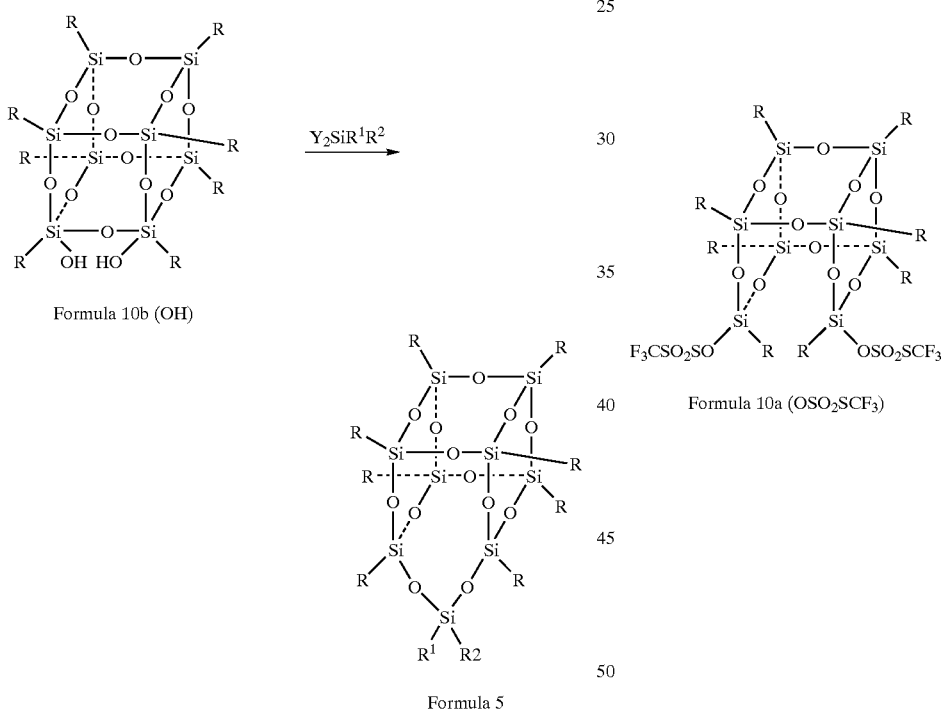

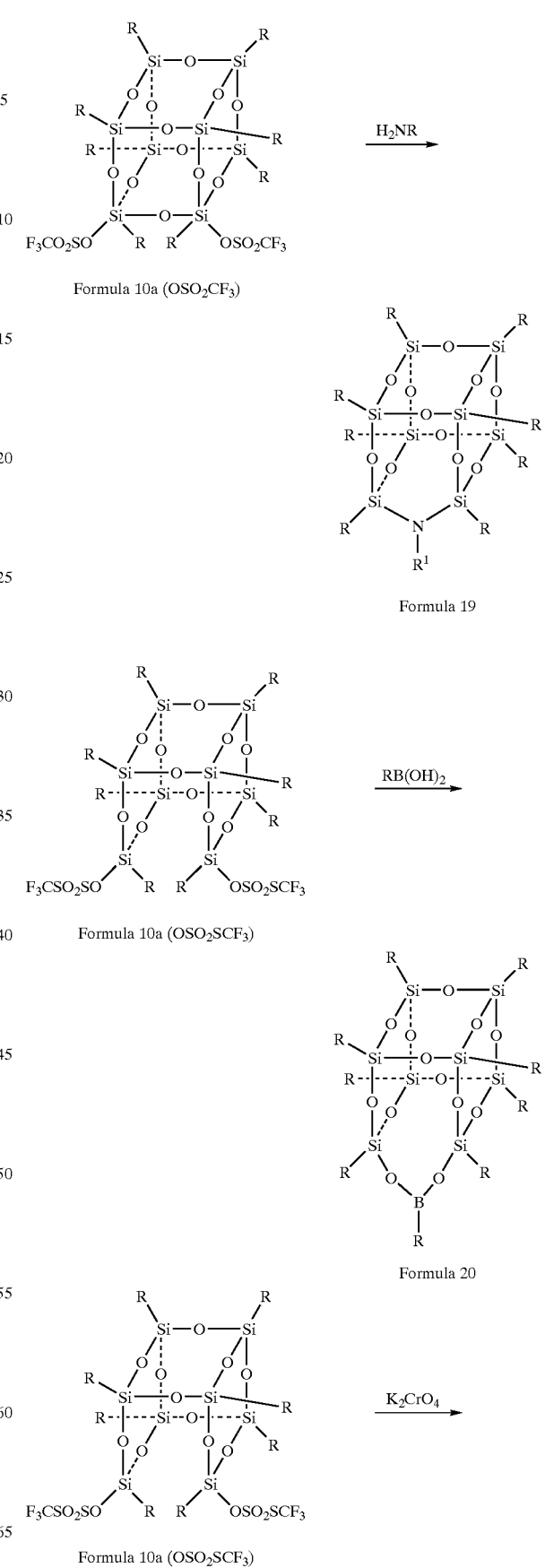

This process can be used to expand the silicon-oxygen frameworks for all sizes of polyhedral oligomeric silsesquioxane cages. The example below shows that the process can be carried out on POSS systems bearing eight silicon atoms within the framework.

SECTION E

Cage Substitutents Other Than Si

The silicon-oxygen frameworks of compounds such as formula 10 can also be selectively expanded by atoms other than silicon. For examples Sn, S, N, P, B, and metals such as Cr, Ti, Zr, Ru, Mo, W, Pt, Pd, Al, Ga and Fe, can readily be incorporated into the silicon oxygen frameworks as indicated below.

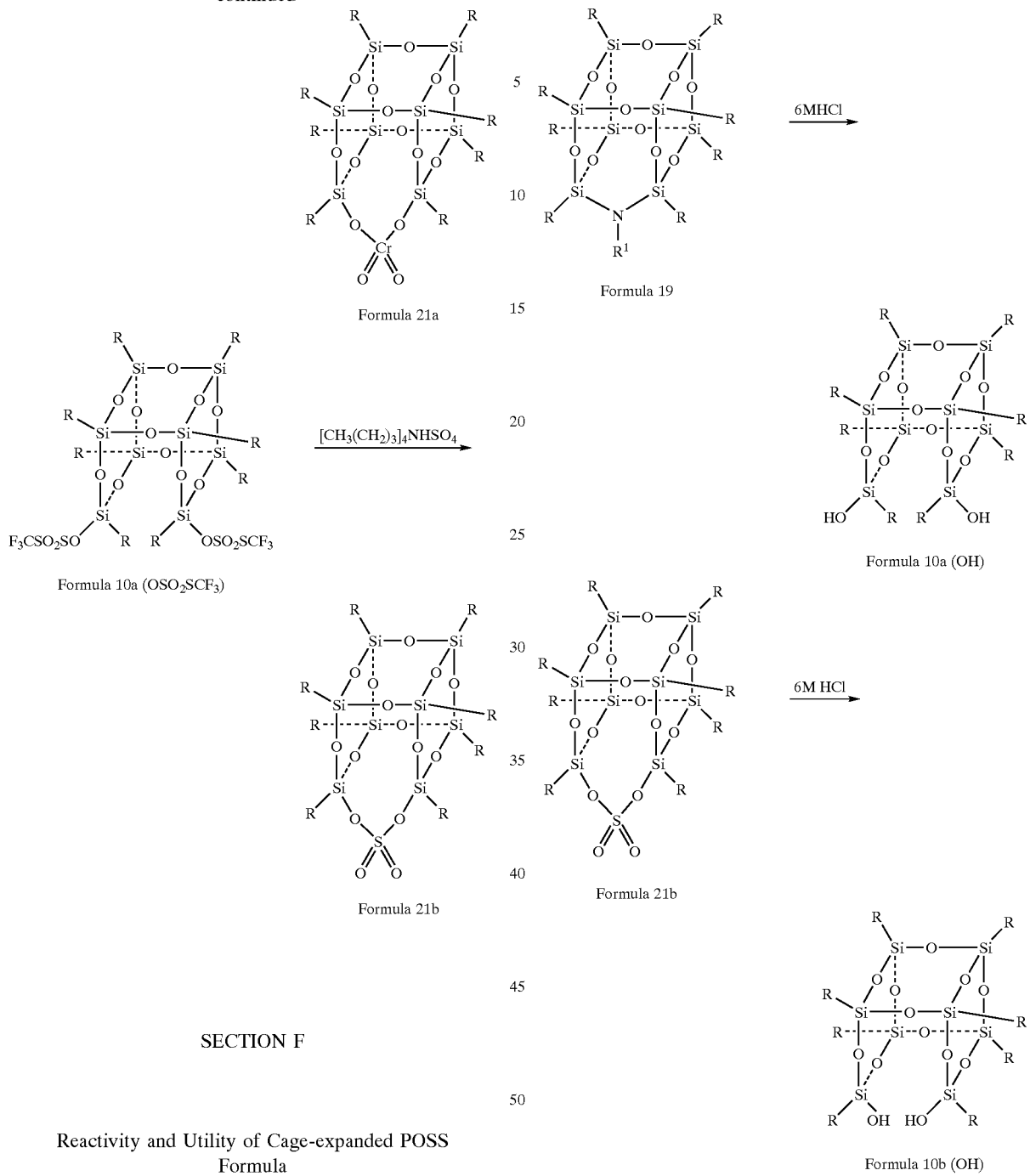

SECTION F

Reactivity and Utility of Cage-expanded POSS Formula

This shows that these cage-expanded compounds (formulas 19–21) can be utilized as chemical reagents to regenerate silanols or they can be used directly as reagents in grafting or polymerizations or as ligands. Note that in the case of using these reagents for the production of silanols, additional stereochemical control can be obtained with respect to whether endo or exo stereochemistry will result. For example treatment of Formula 19 or Formula 20 with concentrated hydrochloric acid produces two different stereochemical isomers of the same compound.

The following examples serve to illustrate the methods of the present invention and should not be construed in limitation thereof.

In such examples: $CHCl_3$ and $CDCl_3$ were distilled over $CaH_2$ prior to use. All other solvents were used as purchased without purification. $HBF_4.OMe_2$ was purchased commercially and used without further purification. $BF_3.OEt_2$ was prepared by bubbling $BF_3$ into a solution of dry $OEt_2$, and then distilled under reduced pressure. $Me_3SnOH$ was prepared by reacting an ether solution of $Me_3SnCl$ with aqueous sodium hydroxide; the white precipitate was filtered and dried in vacuum (0.001 Torr, 23° C.) prior to use. Trifluoromethanesulfonic, methanesulfonic and chlorosulfonic acids were distilled over $P_2O_5$. Trifluoromethanesulfonic anhydride was prepared by stirring trifluoromethanesulfonic acid over $P_2O_5$ and was distilled under reduced pressure. Methyl 3,3-dimethyl-4-pentenoate was distilled over $CaH_2$.

Manipulation of POSS Silicon-oxygen Frameworks

EXAMPLE 1

Preparation of exo-$[(c-C_6H_{11}SiO_{1.5})_4(c-C_6H_{11}(F)SiO_{1.0})_2]_{\Sigma 6}$ (Formula 7)

To a solution of $[(c-C_6H_{11}SiO_{1.5})_6]_{\Sigma 6}$ (Formula 1) (2.038 g, 2.51 mmol) in 15 mL of $CHCl_3$ was added a mixture of $HBF_4 \cdot OMe_2$ (0.460 mL, 3.77 mmol) and $BF_3 \cdot OEt_2$ (0.720 mL, 5.65 mmol). After 10 h at room temperature, the volume was reduced to ~5 mL in vacuo and 5 mL of $CH_3CN$ was added. Formation of two phases was noted. The solution was reduced again to ~3 mL. The white precipitate was collected by filtration and rinsed with copious amount of $CH_3CN$. A second washing with $CH_3CN$ was done by dissolving the crude product mixture in $CH_3Cl$ and reprecipitating with $CH_3CN$ as described above. Spectroscopic analysis ($^1H$, $^{13}C$, $^{29}Si$ NMR) at this point indicated the presence of unreacted $[(c-C_6H_{11}SiO_{1.5})_6]_{\Sigma 6}$ (Formula 1) (8.1%), exo-$[(c-C_6H_{11}SiO_{1.5})_2(c-C_6H_{11}(F)SiO_{1.0})_4]_{\Sigma 6}$ (Formula 8) (13.6%) exo-$[(c-C_6H_{11}SiO_{1.5})_2(c-C_6H_{11}(F)SiO_{1.0})_4]_{\Sigma 6}$ (Formula 9) (0.2%), exo-$[(c-C_6H_{11}SiO_{1.5})_4(c-C_6H_{11}(F)SiO_{1.0})_2]_{\Sigma 6}$ (Formula 7) (67.9%) and exo-endo-$[(c-C_6H_{11}SiO_{1.5})_4(c-C_6H_{11}(F)SiO_{1.0})_1(c-C_6H_{11}(HO)SiO_{1.0})_1]_{\Sigma 6}$ (Formula 7) (10.2%). Slow evaporation of a $CH_3Cl/CH_3CN$ solution of the crude product afforded 735 mg of (13:87) mixture of $[(c-C_6H_{11}SiO_{1.5})_6]_{\Sigma 6}$ (Formula 1) and exo-$[(c-C_6H_{11}SiO_{1.5})_4(c-C_6H_{11}(F)SiO_{1.0})_2]_{\Sigma 6}$ (Formula 7).

EXAMPLE 2

Preparation of exo-$[(c-C_6H_{11}SiO_{1.5})_2(c-C_6H_{11}(F)SiO_{1.0})_4]_{\Sigma 6}$ (Formula 8)

The reaction was performed as described as in Example 1 using $[(c-C_6H_{11}SiO_{1.5})_6]_{\Sigma 6}$ (Formula 1) (1.005 g, 1.24 mmol), $HBF_4 \cdot OMe_2$ (1.2 mL, 9.86 mmol) and $BF_3 \cdot OEt_2$ (1.9 mL, 14.99 mmol) in 15 mL of $CHCl_3$ (room temp, 3.5 h). Spectroscopic analysis ($^1H$, $^{13}C$, $^{29}Si$ NMR) of the crude reaction product indicated the presence of exo-$[(c-C_6H_{11}SiO_{1.5})_2(c-C_6H_{11}(F)SiO_{1.0})_4]_{\Sigma 6}$ (Formula 8) (92%) and exo-$[(c-C_6H_{11}SiO_{1.5})_2(c-C_6H_{11}(F)SiO_{1.0})_4]_{\Sigma 6}$ (Formula 9) (8%). Pure exo-$[(c-C_6H_{11}SiO_{1.5})_2(c-C_6H_{11}(F)SiO_{1.0})_4]_{\Sigma 6}$ (Formula 8) was obtained by crystallization in acetone at 5° C. Yield: 515 mg (48%). exo-$[(c-C_6H_{11}SiO_{1.5})_2(c-C_6H_{11}(F)SiO_{1.0})_4]_{\Sigma 6}$ (Formula 8.

EXAMPLE 3

Preparation of exo-$[(c-C_6H_{11}SiO_{1.5})_2(c-C_6H_{11}(F)SiO_{1.0})_4]_{\Sigma 6}$ (Formula 9)

The reaction was performed as described as in Example 1 to prepare exo-$[(c-C_6H_{11}SiO_{1.5})_2(c-C_6H_{11}(F)SiO_{1.0})_4]_{\Sigma 6}$ (Formula 9): $^{13}C\{^1H\}$ NMR (125 MHz, $CDCl_3$, 25° C.).

EXAMPLE 4

Preparation of exo-endo-$[(c-C_6H_{11}SiO_{1.5})_4(c-C_6H_{11}(F)SiO_{1.0})_1(c-C_6H_{11}(HO)SiO_{1.0})_1]_{\Sigma 6}$ (Formula 7)

The reaction was performed as described as in Example 1 to prepare exo-endo-$[(c-C_6H_{11}SiO_{1.5})_4(c-C_6H_{11}(F)SiO_{1.0})_1(c-C_6H_{11}(HO)SiO_{1.0})_1]_{\Sigma 6}$ (Formula 7).

EXAMPLE 5

Preparation of exo-$[(c-C_6H_{11}SiO_{1.5})_6(c-C_6H_{11}(F)SiO_{1.0})_2]_{\Sigma 8}$ (Formula 10)

(a) To a solution of $[(c-C_6H_{11}SiO_{1.5})_8]_{\Sigma 8}$ (Formula 2) (60.0 mg, 0.055 mmol) in 0.5 mL of $CDCl_3$ was added a mixture of $HBF_4 \cdot OMe_2$ (33.7 mg, 0.253 mmol) and $BF_3 \cdot OEt_2$ (55.2 mg, 0.389 mmol). After 3.5 h at room temperature, spectroscopic analysis ($^1H$, $^{13}C$, $^{29}Si$ NMR) indicated the presence of exo-$[(c-C_6H_{11}SiO_{1.5})_6(c-C_6H_{11}(F)SiO_{1.0})_2]_{\Sigma 8}$ (Formula 10) (44%) and unreacted $[(c-C_6H_{11}SiO_{1.5})_8]_{\Sigma 8}$ (Formula 2) (56%). The ratio of exo-$[(c-C_6H_{11}SiO_{1.5})_6(c-C_6H_{11}(F)SiO_{1.0})_2]_{\Sigma 8}$ (Formula 10) to $[(c-C_6H_{11}SiO_{1.5})_8]_{\Sigma 8}$ (Formula 2) increased to (85:15) after refluxing for 1.5 h, but was unchanged by further heating.

(b) To a solution of $[(c-C_6H_{11}SiO_{1.5})_8]_{\Sigma 8}$ (Formula 2) (1.172 g, 1.083 mmol) in $CH_3Cl$ (12 mL) was added a mixture of $HBF_4 \cdot OMe_2$ (0.730 g, 5.453 mmol) and $BF_3 \cdot OEt2$ (1.230 g, 8.666 mmol). The mixture was heated at 30° C. for 2 h then the solvent was removed under reduced pressure (1 Torr). The residue was washed with excess $CH_3CN$ and dried in vacuo (25° C., 1 Torr) to afford 1.048 g of white solid. Spectroscopic analysis ($^1H$, $^{13}C$, $^{29}Si$ NMR) at this point indicated the presence of unreacted $[(c-C_6H_{11}SiO_{1.5})_8]_{\Sigma 8}$ (Formula 2) (57%) and exo-$[(c-C_6H_{11}SiO_{1.5})_6(c-C_6H_{11}(F)SiO_{1.0})_2]_{\Sigma 8}$ (Formula 10) (43%). Pure exo-$[(c-C_6H_{11}SiO_{1.5})_6(c-C_6H_{11}(F)SiO_{1.0})_2]_{\Sigma 8}$ (Formula 10) was isolated via adsorption chromatography ($SiO_2$, hexanes, $R_f$=0.51).

EXAMPLE 6

Preparation of exo-$[(c-C_6H_{11}SiO_{1.5})_6(c-C_6H_{11}(F_3CO_2SO)SiO_{1.0})_2]_{\Sigma 8}$ (Formula 10a)

To a solution of $[(c-C_6H_{11}SiO_{1.5})_8]_{\Sigma 8}$ (Formula 2) (1.151 g 1.064 mol) in benzene (12 mL) was added triflic acid (0.977 mg, 6.510 mmol) at room temperature. After 45 min., the organic layer was decanted from the triflic acid layer, mixed with hexane (40 mL), and then cooled to ~30° C. for 1 h. The organic layer was again decanted from any residual triflic acid and evaporated (25° C., 1 Torr) to afford exo-$[(c-C_6H_{11}SiO_{1.5})_6(c-C_6H_{11}(F_3CO_2SO)SiO_{1.0})_2]_{\Sigma 8}$ (Formula 10) as a pale white, very water-sensitive solid. The yield was quantitative.

EXAMPLE 7

Alternate Preparation of exo-$[(c-C_6H_{11}SiO_{1.5})_6(c-C_6H_{11}(F_3CO_2SO)SiO_{1.0})_2]_{\Sigma 8}$ (Formula 10a)

Exo-$[(c-C_6H_{11}SiO_{1.5})_6(c-C_6H_{11}(F_3CO_2SO)SiO_{1.0})_2]_{\Sigma 8}$ (Formula 10a) was prepared by reacting $[(c-C_6H_{11}SiO_{1.5})_8]_{\Sigma 8}$ (Formula 2) and triflic anhydride in $CDCl_3$ at 25° C. for 30 min according to the procedure described above for the synthesis of exo-$[(c-C_6H_{11}SiO_{1.5})_6(c-C_6H_{11}(F_3CO_2SO)SiO_{1.0})_2]_{\Sigma 8}$ (Formula 10a).

EXAMPLE 8

Preparation of exo-twisted-$[(c-C_6H_{11}SiO_{1.5})_6(c-C_6H_{11}(F_3CO_2SO)SiO_{1.0})_2]_{\Sigma 8}$ (Formula 11a)

Exo-twisted-$[(c-C_6H_{11}SiO_{1.5})_6(c-C_6H_{11}(F_3CO_2SO)SiO_{1.0})_2]_{\Sigma 8}$ (Formula 11a) was prepared in 70% yield by reacting $[(c-C_6H_{11}SiO_{1.5})_8]_{\Sigma 8}$ (Formula 2) (102 mg, 0.094 mmol) and TfOH (83 µl, 0.943 mmol) at 25° C. for 3 h according to the procedure described above for the synthesis of exo-$[(c-C_6H_{11}SiO_{1.5})_6(c-C_6H_{11}(F_3CO_2SO)SiO_{1.0})_2]_{\Sigma 8}$ (Formula 10a).

EXAMPLE 9

Preparation of exo-[(c-$C_6H_{11}SiO_{1.5})_2$(c-$C_6H_{11}$ ($H_3CO_2SO)SiO_{1.0})_4]_{\Sigma 6}$ (Formula 8)

Exo-[(c-$C_6H_{11}SiO_{1.5})_2$(c-$C_6H_{11}$($H_3CO_2SO)SiO_{1.0})_4]_{\Sigma 6}$ (Formula 8) was prepared in 70% yield by reacting [(c-$C_6H_{11}SiO_{1.5})_6]_{\Sigma 6}$ (Formula 1) (55.1 mg, 0.068 mmol) and $CH_3SO_3H$ (32.7mg, 0.340 mmol) at 60° C. for 8 h according to the procedure described above for the synthesis of exo-[(c-$C_6H_{11}SiO_{1.5})_4$(c-$C_6H_{11}(F_3CO_2SO)SiO_{1.0})_2]_{\Sigma 6}$ (Formula 8).

EXAMPLE 10

Preparation of exo-[($C_2H_5SiO_{1.5})_6(C_2H_5(ClO_2SO)SiO_{1.0})_2]_{\Sigma 8}$ (Formula 10a)

Exo-[($C_2H_5SiO_{1.5})_6(C_2H_5(ClO_2SO)SiO_{1.0})_2]_{\Sigma 8}$ (Formula 10a) was prepared in 31% yield by reacting [($C_2H_5 SiO_{1.5})_8]_{\Sigma 8}$ (Formula 2) (72.4 mg, 0.112 mmol), $ClO_3H$ (11.0 mg, 0.094 mmol) at 25° C. for 15 min according to the procedure described above for the synthesis of exo-[($C_2H_5SiO_{1.5})_6(C_2H_5(ClO_2SO)SiO_{1.0})_2]_{\Sigma 8}$ (Formula 10a).

EXAMPLE 11

Preparation of exo-[($CH_2$=$CHSiO_{1.5})_6(CH_2$=$CH)(F)SiO_{1.0})_2]_{\Sigma 8}$ (Formula 10a)

Exo-[($CH_2$=$CH)_8Si_8O_{11}F_2$] (Formula 10a) was prepared in 37% by reacting [($CH_2$=$CHSiO_{1.5})_8]_{\Sigma 8}$ (66.7 mg, 0.105 mmol), $HBF_4.OMe_2$ (39.7 mg, 0.297 mmol) and $BF_3.OEt_2$ (25.4 mg, 0.179 mmol) at 25° C. for 1 h according to the procedure described above for the synthesis of exo-[(c-$C_6H_{11}SiO_{1.5})_6$(c-$C_6H_{11})(F)SiO_{1.0})_2]_{\Sigma 8}$ (Formula 10a).

EXAMPLE 12

Preparation of exo-[($C_2H_5SiO_{1.5})_6(C_2H_5)(F)SiO_{1.0})_2]_{\Sigma 8}$ (Formula 10a)

EXo-[($C_2H_5SiO_{1.5})_6(C_2H_5)(F)SiO_{1.0})_2]_{\Sigma 8}$ (Formula 10a) was prepared in 80% by reacting [($C_2H_5SiO_{1.5})_8]_{\Sigma 8}$ (Formula 2) (47 mg, 0.072 mmol), $HBF_4.OMe_2$ (41 mg, 0.308 mmol) and $BF_3.OEt_2$ (63 mg, 0.444 mmol) at 25° C. for 1 h according to the procedure described above for the synthesis of exo-[($C_2H_5SiO_{1.5})_6(C_2H_5)(F)SiO_{1.0})_2]_{\Sigma 8}$ (Formula 10a).

EXAMPLE 13

Preparation of exo-[(p-$CH_3C_6H_4SiO_{1.5})_6$(p-$CH_3C_6H_4)(F)SiO_{1.0})_2]_{\Sigma 8}$ (Formula 10a)

Exo-[(p-$CH_3C_6H_4SiO_{1.5})_6$(p-$CH_3C_6H_4)(F)SiO_{1.0})_2]_{\Sigma 8}$ (Formula 10a) was prepared in 80% by reacting exo-[(p-$CH_3C_6H_4SiO_{1.5})_8]_{\Sigma 8}$ (Formula 2) (80.6 mg, 0.070 mmol), $HBF_4.OMe_2$ (43.1 mg, 0.322 mmol) and $BF_3.OEt_2$ (61.6 mg, 0.434 mmol) at 25° C. for 3 h according to the procedure described above for the synthesis of exo-[(p-$CH_3C_6H_4SiO_{1.5})_6$(p-$CH_3C_6H_4)(F)SiO_{1.0})_2]_{\Sigma 8}$ (Formula 10a).

EXAMPLE 14

Preparation of exo-[($CH_3SiO_{1.5})_8(CH_3)(F)SiO_{1.0})_2]_{\Sigma 10}$ (Formula 14)

Exo-[($CH_3SiO_{1.5})_8(CH_3)(F)SiO_{1.0})_2]_{\Sigma 10}$ (Formula 14) was prepared in 24% yield by reacting [($CH_3SiO_{1.5})_{10}]_{\Sigma 10}$ (Formula 3) (31.2 mg, 0.046 mmol), $HBF_4.OMe_2$ (12.4 mg, 0.093 mmol) and $BF_3.OEt_2$ (23.5 mg, 0.166 mmol) at 25° C. for 40 min according to the procedure described above for the synthesis of exo-[(c-$C_6H_{11}SiO_{1.5})_6$(c-$C_6H_{11})(F)SiO_{1.0})_2]_{\Sigma 8}$ (Formula 10a).

EXAMPLE 15

Preparation of exo-[(c-$C_6H_{11}SiO_{1.5})_{10}$(c-$C_6H_{11})(F)SiO_{1.0})_2]_{\Sigma 12}$ (Formulas 15a and 15b)

Exo-[(c-$C_6H_{11}SiO_{1.5})_{10}$(c-$C_6H_{11})(F)SiO_{1.0})_2]_{\Sigma 12}$ (Formula 15) was prepared in 70% overall yield by reacting xo-[(c-$C_6H_{11}SiO_{1.5})_{12}]_{\Sigma 12}$ (Formula 4) (53.0 mg, 0.033 mmol), $HBF_4.OMe_2$ (26.0 mg, 0.194 mmol) and $BF_3.OEt_2$ (38.5 mg, 0.271 mmol) at 60° C. for 2 h according to the procedure described above for the synthesis of exo-[(c-$C_6H_{11}SiO_{1.5})_6$(c-$C_6H_{11})(F)SiO_{1.0})_2]_{\Sigma 8}$ (Formula 10a).

EXAMPLE 16

Preparation of exo-[(c-$C_6H_{11}SiO_{1.5})_6(C_6H_5CH_2)(F)SiO_{1.0})_1(C_6H_5CH_2)(F)SiO_{1.0})_1]_{\Sigma 8}$ (Formula 11)

A mixture of isomers of exo-[(c-$C_6H_{11}SiO_{1.5})_6(C_6H_5CH_2)(F)SiO_{1.0})_1(C_6H_5CH_2)(F)SiO_{1.0})_1]_{\Sigma 8}$ (Formula 11) was prepared in 66% yield by reacting [(c-$C_6H_{11}SiO_{1.5})_6(C_6H_5CH_2)SiO_{1.5})_1]_{\Sigma 8}$ (Formula 6) (60.8 mg, 0.056 mmol), $HBF_4.OMe_2$ (32.2 mg, 0.241 mmol) and $BF_3.OEt_2$ at 60° C. for 15 h according to the procedure described above for the synthesis of exo-[(c-$C_6H_{11}SiO_{1.5})_6(C_6H_5CH_2)(F)SiO_{1.0})_1(C_6H_5CH_2)(F)SiO_{1.0})_1]_{\Sigma 8}$ (Formula 11).

EXAMPLE 17

Preparation of Exo-[(c-$C_5H_9SiO_{1.5})_6(C_5H_9)(F)SiO_{1.0})_1(CH_3)(F)SiO_{1.0})_1]_{\Sigma 8}$ (Formula 12a)

Isomer A of Exo-[(c-$C_5H_9SiO_{1.5})_6(C_5H_9)(F)SiO_{1.0})_1(CH_3)(F)SiO_{1.0})_1]_{\Sigma 8}$ (Formula 12a) was prepared in 33% yield by reacting [(c-$C_5H_9SiO_{1.5})_7(CH_3)SiO_{1.5})_1]_{\Sigma 8}$ (Formula 6) (68.4 mg, 0.075 mmol), $HBF_4.OMe_2$ (20.3 mg, 0.152 mmol) and $BF_3.OEt_2$ (50.3 mg, 0.354 mmol) at 25° C. for 2 h according to the procedure described above for the synthesis of exo-[(c-$C_5H_9SiO_{1.5})_6(C_5H_9)(F)SiO_{1.0})_1(CH_3)(F)SiO_{1.0})_1]_{\Sigma 8}$ (Formula 10a).

EXAMPLE 18

Preparation of endo-twisted-[(c-$C_6H11SiO_{1.5})_6$((c-$C_6H_{11})(HO)SiO_{1.0})_2]_{\Sigma 8}$ (Formula 11b)

Endo-twisted-[(c-$C_6H_{11}SiO_{1.5})_6$((c-$C_6H_{11})(HO)SiO_{1.0})_2]_{\Sigma 8}$ (Formula 11b) was prepared in 70% yield by hydrolyzing exo-twisted-[(c-$C_6H11SiO_{1.5})_6$((c-$C_6H_{11})(HO)SiO_{1.0})_2]_{\Sigma 8}$ (Formula 11a) according to the procedure described above for the synthesis of endo-[(c-$C_6H_{11}SiO_{1.5})_6$((c-$C_6H_{11})(HO)SiO_{1.0})_2]_{\Sigma 8}$ (Formula 10a). The product was identical to a sample of endo-twisted-[(c-$C_6H_{11}SiO_{1.5})_6$((c-$C_6H_{11})(HO)SiO_{1.0})_2]_{\Sigma 8}$ (Formula 11b) prepared from exo-twisted-[(c-$C_6H_{11}SiO_{1.5})_6$((c-$C_6H_{11})(HO)SiO_{1.0})_2]_{\Sigma 8}$ (Formula 11a) via sequential reactions with $HBF_4$/$BF_3$, $Me_3SnOH$ and 6N HCl (i.e., the established three-step procedure for inverting stereochem of Si—OH groups).

EXAMPLE 18.5

Preparation of [(c-$C_6H_{11}SiO_{1.5})_4$((c-$C_6H_{11})(HO)SiO_{1.0})_2]_{\Sigma 6}$ (Formula 7d)

A solution of $CH_3SO_3H$ (2.33 g, 24.3 mmol) in $CHCl_3$ was added to a solution of [(c-$C_6H_{11}SiO_{1.5})_6]_{\Sigma 6}$ (Formula 1)

(3.90 g, 4.80 mmol) in CHCl$_3$. The reaction mixture was heated for 4 h at 70° C. with stirring. Evaporation of the solvent (0.1 Torr, 25° C.) afforded a white microcrystalline solid (4.22 g, 89% crude yield). A 1.511 g sample of the crude product was stirred in pyridine (~6 mL) for 10 minutes and filtered to remove any unreacted [(c-C$_6$H$_{11}$SiO$_{1.5}$)$_6$]$_{\Sigma 6}$ (Formula 1). [(c-C$_6$H$_{11}$SiO$_{1.5}$)$_4$((c-C$_6$H$_{11}$)(HO)SiO$_{1.0}$)$_2$]$_{\Sigma 6}$ (Formula 7d) precipitated from the filtrate upon addition of CH$_3$CN (40 mL) to afford a white powder, which was dissolved in Et$_2$O and washed with 6N HCl. Drying over MgSO$_4$ and evaporation of the solvent (2 mL) afforded a white solid, which was recrystallized from CCl$_4$ to afford the product as colorless crystals (584 mg, 39%).

EXAMPLE 19

Preparation of Exo-twisted-[(C$_2$H$_5$SiO$_{1.5}$)$_6$((C$_2$H$_5$) (HO$_3$SO)SiO$_{1.0}$)$_2$]$_{\Sigma 8}$ (Formula 11a) and Exo- [(C$_2$H$_5$SiO$_{1.5}$)$_6$((C$_2$H$_5$)(HO$_3$SO)SiO$_{1.0}$)$_2$]$_{\Sigma 8}$ (Formula 10a)

A mixture of exo-twisted-[(C$_2$H$_5$SiO$_{1.5}$)$_6$((C$_2$H$_5$) (HO$_3$SO)SiO$_{1.0}$)$_2$]$_{\Sigma 8}$ (Formula 11a) and exo-[(C$_2$H$_5$SiO$_{1.5}$)$_6$ ((C$_2$H$_5$)(HO$_3$SO)SiO$_{1.0}$)$_2$]$_{\Sigma 8}$ (Formula 10a) (1:3 ratio) was prepared in 27% yield by reacting [(C$_2$H$_5$SiO$_{1.5}$)$_8$]$_{\Sigma 8}$ (Formula 2) (74.8 mg, 0.115 mmol) and cold H$_2$SO$_{4/20}$% SO$_3$ (45.3 mg, 0.389 mmol) at 25° C. for 30 min according to the procedure described above for the synthesis of exo- [(c-C$_6$H$_{11}$SiO$_{1.5}$)$_6$((c-C$_6$H$_{11}$)(F$_3$CO$_2$SO)SiO$_{1.0}$)$_2$]$_{\Sigma 8}$ (Formula 10a).

CONVERSION OF FUNCTIONAL GROUPS AND MANIPULATION OF STEREOCHEMISTRY

EXAMPLE 20

Method 1

Synthesis of endo-[(c-C$_6$H$_{11}$SiO$_{1.5}$)$_6$((c-C$_6$H$_{11}$)(HO) SiO$_{1.0}$)$_2$]$_{\Sigma 8}$ (Formula 10b)

To a solution of exo-[(c-C$_6$H$_{11}$SiO$_{1.5}$)$_6$((c-C$_6$H$_{11}$) (F$_3$CO$_2$SO)SiO$_{1.0}$)$_2$]$_{\Sigma 8}$ (Formula 10a) (1.8 g, 1.33 mmol) in Et$_2$O (13 mL) was added triethylamine (0.281 g, 2.777 mmol) at room temperature. After 15 min, the solution was added with vigorous stirring to a mixture of water (50 mL) and Et$_2$O (50 mL). The organic layer was immediately separated from the aqueous layer and filtered through a small pad of anhydrous magnesium sulfate. Concentration of the solution to ca. 10 mL and addition of acetonitrile afforded a white precipitate, which was collected by filtration, dissolved in CH$_2$Cl$_2$ (150 mL) and reprecipitated with acetonitrile (50 mL). Vacuum filtration and drying in air afforded 0.959 g of white solid containing endo-[(c-C$_6$H$_{11}$SiO$_{1.5}$)$_6$((c-C$_6$H$_{11}$)(HO)SiO$_{1.0}$)$_2$]$_{\Sigma 8}$ (Formula 10b) and [(c-C$_6$H$_{11}$SiO$_{1.5}$)$_6$((c-C$_6$H$_{11}$)(HO)SiO$_{1.0}$)$_2$]$_{\Sigma 8}$ (Formula 2) in a 97:3 ratio.

EXAMPLE 21

Method 1

Preparation of endo-exo-[(c-C$_6$H$_{11}$SiO$_{1.5}$)$_6$((c-C$_6$H$_{11}$)(HO)SiO$_{1.0}$)$_2$]$_{\Sigma 8}$ (Formula 10c)

To a mixture of Et$_2$O (3 mL) and water (3 mL) was added a solution of exo-[(c-C$_6$H$_{11}$SiO$_{1.5}$)$_6$((c-C$_6$H$_{11}$)(F$_3$CO$_2$SO) SiO$_{1.0}$)$_2$]$_{\Sigma 8}$ (Formula 10a) (72.6 mg, 0.053 mmol) and triethylamine (8.6 mg, 0.085) in Et$_2$O (3 mL) with a vigor-ous stirring. After 5 min, the organic layer was separated and dried over MgSO$_4$; addition of CH$_3$CN (6 mL) and reduction of the volume to ca. 5 mL precipitated a white solid (yield 58 mg). Spectroscopic analysis indicate a mixture of endo-exo-[(c-C$_6$H$_{11}$SiO$_{1.5}$)$_6$((c-C$_6$H$_{11}$)(HO)SiO$_{1.0}$)$_2$]$_{\Sigma 8}$ (Formula 10c) (46%) and endo-[(c-C$_6$H$_{11}$SiO$_{1.5}$)$_6$((c-C$_6$H$_{11}$)(HO)SiO$_{1.0}$)$_2$]$_{\Sigma 8}$ (Formula 10b) (54%).

EXAMPLE 22

Method 21

A (13:87) mixture of [(c-C$_6$H$_{11}$SiO$_{1.5}$)$_6$]$_{\Sigma 6}$ (Formula 1) and exo-[(c-C$_6$H$_{11}$SiO$_{1.5}$)$_4$((c-C$_6$H$_{11}$)(F)SiO$_{1.0}$)$_2$]$_{\Sigma 6}$[(c-C$_6$H$_{11}$)$_6$Si$_6$O$_8$F$_2$] (Formula 7) (300 mg) was reacted with excess Me$_3$SnOH (630 mg, 3.48 mmol) in refluxing CHCl$_3$ (30 mL) for 11 h. The volatiles were removed in vacuo to afford a white solid, which was redissolved in C$_6$H$_6$ (25 mL) and filtered to remove particulate. After removing the solvent under vacuo, the solid was dissolved in CH$_3$Cl (15 mL) and stirred with a solution of aqueous HCl (1.6 mL of I.2M). After 30 min, the mixture was dried over MgSO$_4$, filtered and evaporated (0.1 Torr) to afford an amorphous white foam, which was extracted with pyridine (1 mL, 30 min). ([(c-C$_6$H$_{11}$SiO$_{1.5}$)$_6$]$_{\Sigma 6}$ is insoluble in pyridine.) Careful addition of the pyridine extract to an ice-cold solution of HCl (2.5 mL of concentrated HCl and 2 mL of water) precipitated the disilanol, which was washed with water, extracted with CH$_2$Cl$_2$, dried over MgSO$_4$, and evaporated to afford exo-[(c-C$_6$H$_{11}$SiO$_{1.5}$)$_4$((c-C$_6$H$_{11}$)(HO)SiO$_{1.0}$)$_2$]$_{\Sigma 6}$ [(c-C$_6$H$_{11}$)$_6$Si$_6$O$_8$(OH)$_2$] (Formula 7) as a white solid in quantitative yield based on available exo-[(c-C$_6$H$_{11}$SiO$_{1.5}$)$_4$ ((c-C$_6$H$_{11}$)(F)SiO$_{1.0}$)$_2$]$_{\Sigma 6}$ (Formula 7).

EXAMPLE 23

Method 2

Synthesis of Exo-[(c-C$_6$H$_{11}$SiO$_{1.5}$)$_6$((c-C$_6$H$_{11}$)(HO) SiO$_{1.0}$)$_2$]$_{\Sigma 8}$ (Formula 10a)

Using the procedure described from the conversion of [(c-C$_6$H$_{11}$SiO$_{1.5}$)$_4$((c-C$_6$H$_{11}$)(F)SiO$_{1.0}$)$_2$]$_{\Sigma 6}$ (Formula 7) to [(c-C$_6$H$_{11}$SiO$_{1.5}$)$_4$((c-C$_6$H$_{11}$)(HO)SiO$_{1.0}$)$_2$]$_{\Sigma 6}$ (Formula 7) a 0.910 g sample containing exo-[(c-C$_6$H$_{11}$SiO$_{1.5}$)$_6$((c-C$_6$H$_{11}$) (F)SiO$_{1.0}$)$_2$]$_{\Sigma 8}$ (Formula 10) (43%) and [(c-C$_6$H$_{11}$ SiO$_{1.5}$)$_8$]$_{\Sigma 8}$ (Formula 2) (57%) was reacted sequentially with Me$_3$SnOH (0.807 g) and 6N HCl (2 mL) in CHCl$_3$ (10 mL). After evaporating the majority of volatiles under reduced pressure (25° C., 1 Torr), the mixture was separated by flash chromatography on silica gel. (Both [(c-C$_6$H$_{11}$SiO$_{1.5}$)$_8$]$_{\Sigma 8}$ (Formula 2) and exo-[(c-C$_6$H$_{11}$SiO$_{1.5}$)$_6$((c-C$_6$H$_{11}$)(HO) SiO$_{1.0}$)$_2$]$_{\Sigma 8}$ (Formula 12) are soluble in pyridine.) Unreacted [(c-C$_6$H$_{11}$SiO$_{1.5}$)$_8$]$_{\Sigma 8}$ (Formula 2) (511 mg) was eluted first with hexane. Subsequent elution with 1:1 (v/v) CH$_2$Cl$_2$/ hexane afforded pure exo-[(c-C$_6$H$_{11}$SiO$_{1.5}$)$_6$((c-C$_6$H$_{11}$)(HO) SiO$_{1.0}$)$_2$]$_{\Sigma 8}$ (Formula 10a) as a white solid (268 mg, 68% based on available difluoride) after evaporation (25° C., 1 Torr).

EXPANSION AND REDUCTION OF POSS SILICON-OXYGEN FRAMEWORKS

EXAMPLE 24

Preparation of [(c-C$_6$H$_{11}$SiO$_{1.5}$)$_8$((CH$_3$)(H) SiO$_{1.0}$)$_1$]$_{\Sigma 9}$ (Formula 5)

Triethylamine (0.070 g, 0.691 mmol) and Cl$_2$Si(H)Me (0.029 g, 0.253 mmol) were added to a solution of endo-

[(c-$C_6H_{11}$Si$O_{1.5}$)$_6$((c-$C_6H_{11}$)(HO)Si$O_{1.0}$)$_2$]$_{\Sigma 8}$ (Formula 10b) (0.245 g, 0.223 mmol) in cold Et$_2$O (5 mL). (The sample of endo-[(c-$C_6H_{11}$)$_8$Si$_8O_{11}$(OH)$_2$] contained 3% [(c-$C_6H_{11}$)$_8$Si$_8O_{12}$].) Precipitation of Et$_3$N.HCl began immediately, but the reaction was stirred 4 h at 25° C. before filtration and concentration of the filtrate to ca. 1 mL. Complete precipitation of Et$_3$N.HCl was induced by adding benzene (2 mL) and cooling to 0° C. Filtration of the resulting solution through celite and evaporation (25° C., 1 Torr) afforded a white solid. Pure [(c-$C_6H_{11}$Si$O_{1.5}$)$_8$((CH$_3$)(H)Si$O_{1.0}$)$_1$]$_{\Sigma 9}$ (Formula 5) was obtained in 76% yield (189 mg) by flash chromatography (SiO$_2$, hexanes, Rf=0.52).

EXAMPLE 25

Preparation of [(c-$C_5H_9$Si$O_{1.5}$)$_4$((c-$C_5H_9$)(HO)Si$O_{1.0)3}$]$_{\Sigma 7}$ (Formula 13a)

In a typical reaction, 107 g (114 mmol) of [(c-$C_5H_9$Si$O_{1.5}$)$_7$((Cl)Si$O_{1.5}$)$_1$]$_{\Sigma 8}$ (Formula 6) is dissolved in 800 mL of tetrahydrofuran (THF) and the solution is kept under nitrogen. To this well-stirred solution, an excess of LiAlH$_4$ (typically about 8 to 10 grams) is added over about 30 minutes. After stirring for another 60 minutes, the solution is filtered (in air) and the filtrate solvent removed under vacuum. The resulting solid is extracted with 500 mL of warm hexanes and the suspension filtered. The filtrate solution is reduced in volume under vacuum to form a slurry, that is then added to 600 mL of well-stirred methanol. After several hours of stirring, the methanol-insoluble precipitate is collected by filtration to yield, after drying, 50–60 grams of [(c-$C_5H_9$Si$O_{1.5}$)$_7$((H)Si$O_{1.5}$)$_1$]$_{\Sigma 8}$ (Formula 3). The methanol-soluble filtrate is evaporated to dryness, then dissolved in 200 mL of THF and 100 mL of diethyl ether. This solution is twice washed with 100 mL of 1M aqueous HCl, followed by washings with 100 mL of water and 100 mL of a saturated aqueous NaCl solution. The organic solution is dried over MgSO$_4$, filtered and the filtrate solvent removed under vacuum. The solid is then extracted with 50 mL of THF and the resulting slurry is added to approximately 200 mL of well-stirred acetone. After 1 hour of stirring, the precipitate is collected by filtration to yield, after drying, 7–15 grams of [(c-$C_5H_9$Si$O_{1.5}$)$_4$((c-$C_5H_9$)(HO)Si$O_{1.0)3}$]$_{\Sigma 7}$ (Formula 13a). Typical yields of the [(c-$C_5H_9$Si$O_{1.5}$)$_4$((c-$C_5H_9$)(HO)Si$O_{1.0}$)$_3$]$_{\Sigma 7}$ (Formula 13a) product range from 7 to 15%.

EXAMPLE 26

Preparation of [(c-$C_6H_{11}$Si$O_{1.5}$)$_6$(c-$C_6H_{11}$Si$O_{1.0}$)$_2$((PhN))$_1$]$_{\Sigma 9}$ (Formula 19)

To a solution of [(C-$C_6H_{11}$Si$O_{1.5}$)$_6$((c-$C_6H_{11}$)(TfO)Si$O_{1.0}$)$_2$]$_{\Sigma 8}$ (Formula 10a) (159.0 mg, 0.117 mmol) and triethylamine (34.1 mg, 0.337 mmol) in benzene (2 mL) was slowly added a solution of aniline (11.9 mg, 0.128 mmol) in benzene (0.5 mL). After stirring the resulting emulsion for 0.5 h at 25° C., the benzene layer was separated from the ammonium triflate by decantation. The oily ammonium triflate was rinsed twice with benzene (0.5 mL). The organic layer were combined and the solvent was removed under reduced pressure. Precipitation from a mixture of CHCl$_3$/CH$_3$CN affords [(c-$C_6H_{11}$Si$O_{1.5}$)$_6$(c-$C_6H_{11}$Si$O_{1.0}$)$_2$((PhN))$_1$]$_{\Sigma 9}$ as a white solid.

EXAMPLE 27

Preparation of [(c-$C_6H_{11}$Si$O_{1.5}$)$_6$(c-$C_6H_{11}$Si$O_{1.0}$)$_2$((CH$_3$(CH$_2$)$_3$BO$_2$))$_1$]$_{\Sigma 9}$ (Formula 20)

To a solution of exo-[(c-$C_6H_{11}$Si$O_{1.5}$)$_6$((c-$C_6H_{11}$)(F$_3$CO$_2$SO)Si$O_{1.0}$)$_2$]$_{\Sigma 8}$ (Formula 10a) (152.6 mg, 0.112 mmol) and triethylamine (60.8 mg, 0.601 mmol) in benzene (3 mL) was slowly added a solution of butylboronic acid (27.9 mg, 0.274 mmol) in benzene (0.5 mL). After stirring the resulting emulsion for 0.5 h at 25° C., the solvent was removed under vacuum and the residue was dried under vacuum. The residue was redissolved in benzene (1 mL). The benzene layer was separated from the ammonium triflate by decantation. The oily ammonium triflate was rinsed twice with benzene (0.5 mL). The organic layer were combined and the volume of the solvent was concentrated to ca 1 mL. Addition of CH$_3$CN (10 mL) affords a precipitation of a mixture [(c-$C_6H_{11}$Si$O_{1.5}$)$_6$(c-$C_6H_{11}$Si$O_{1.0}$)$_2$((CH$_3$(CH$_2$)$_3$BO$_2$))$_1$]$_{\Sigma 9}$ and [(c-$C_6H_{11}$Si$O_{1.5}$)$_8$]$_{\Sigma 8}$ (81:19) (127 mg).

EXAMPLE 28

Preparation of [(c-$C_6H_{11}$Si$O_{1.5}$)$_6$(c-$C_6H_{11}$Si$O_{1.0}$)$_2$(CrO$_4$)$_1$]$_{\Sigma 9}$ (Formula 21)

A mixture of endo-[(c-$C_6H_{11}$Si$O_{1.5}$)$_6$((c-$C_6H_{11}$)(HO)Si$O_{1.0}$)$_2$]$_{\Sigma 8}$[(c-$C_6H_{11}$)$_8$Si$_8O_{11}$(OH)$_2$]) (Formula 10b) (148 mg, 0.135 mmol), CrO$_3$ (133 mg, 1.330 mmol) and MgSO$_4$ (371 mg) in CCl$_4$ (4 mL) was stirred for 48 h in the dark. Vacuum filtration and evaporation of the volatile material under reduced pressure gave an amorphous orange solid, which was purified by chromatography using a short column of SiO$_2$ (dried under vacuum at 300° C.) and CHCl$_3$ as eluent to give [([(c-$C_6H_{11}$Si$O_{1.5}$)$_6$(c-$C_6H_{11}$Si$O_{1.0}$)$_2$(CrO$_4$)$_1$]$_{\Sigma 9}$) as a bright orange solid in 55% yield.

Thus the present invention discloses methods that enable the selective manipulation of the silicon-oxygen frameworks in polyhedral oligomeric silsesquioxane (POSS) cage molecules. The methods of the invention provide for the selective ring-opening, stereochemical interconversion, expansion and reduction of POSS frameworks to form new families of POSS-related compounds.

Further the present invention teaches processes that enable the manipulation of the silicon-oxygen frameworks (the cage-like structure) of POSS-related compounds into new POSS species bearing frameworks with functionalities thereon for grafting, polymerization, catalysis or other reactions.

What is claimed is:

1. A method for controlling the stereo chemistry of X groups to exo or endo positions on a polyhedral oligomeric silsesquioxane (POSS) compound comprising, adding reagents selected from the group consisting of a) CF$_3$SO$_3$H then H$_2$O, b) Me$_3$SnOH then HCl aq and c) HBF$_4$/BF$_3$ then Me$_3$SnOH then HCl aq to said X groups to change one or more positions thereof to endo or exo, wherein said POSS compound is of the formula [(RSi$O_{1.5}$)$_m$(RXSi$O_{1.0}$)$_n$]$_{\Sigma \#}$, n=4–24, m=1–12, $\Sigma$=nanostructure, # is m+n, R is aliphatic, aromatic, olefinic, alkoxy, siloxy or H and said X groups are selected from the group consisting of OH, OSO$_2$, CF$_3$, OSO$_2$, CH$_3$, F, Cl, I, Br, Me$_3$SnO, alkoxy, siloxy and Me$_3$ is (CH$_3$)$_3$ and aq is aqueous.

2. The method of claim 1 wherein an X group can change in kind as well as in said positions.

3. The method of claim 1 wherein

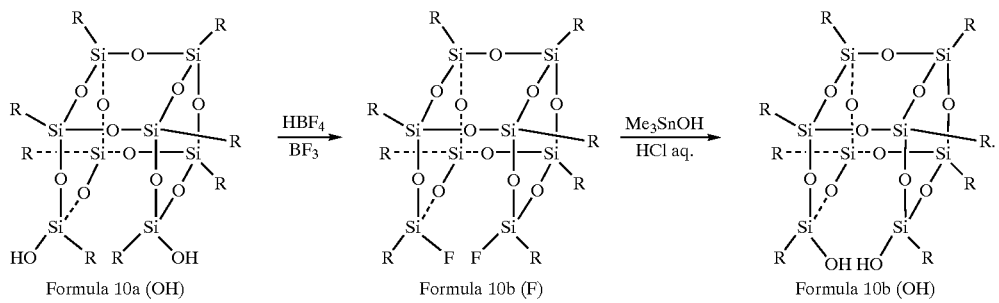
4. The method in claim 1 wherein
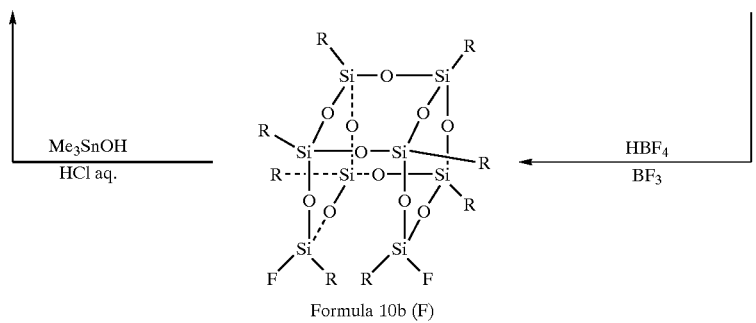
5. The method of claim 1 wherein
-continued
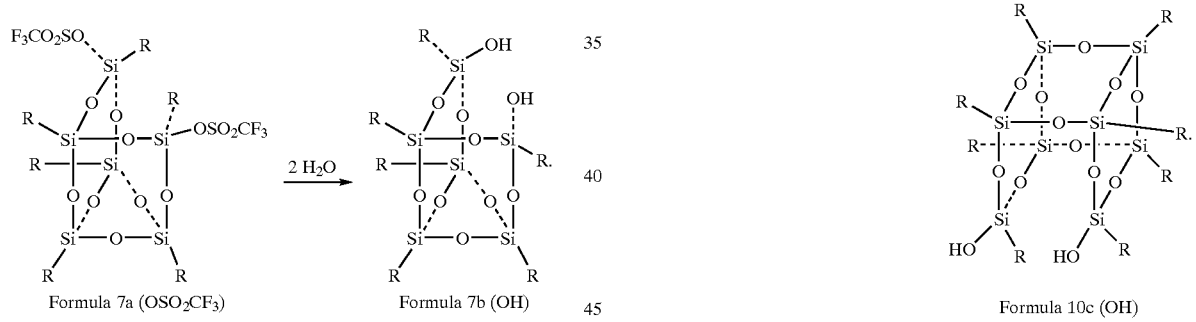
6. The method of claim 1 wherein
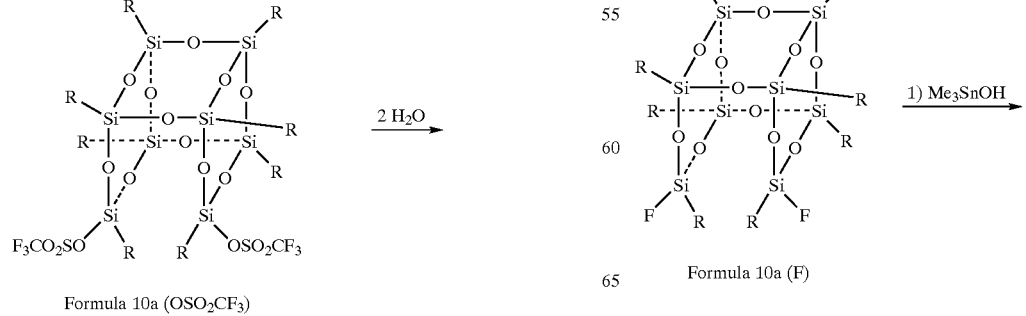

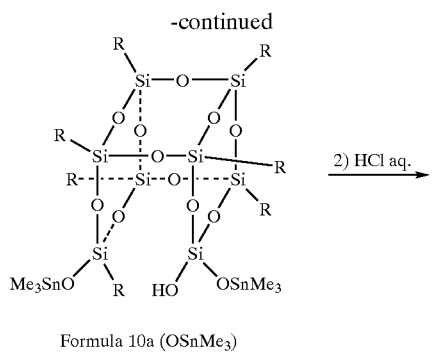
Formula 10a (OSnMe₃)
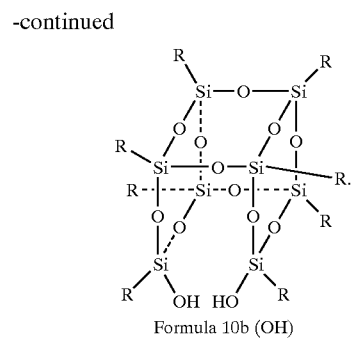
Formula 10b (OH)
Formula 10a (OH)
7. The method of claim 1 wherein
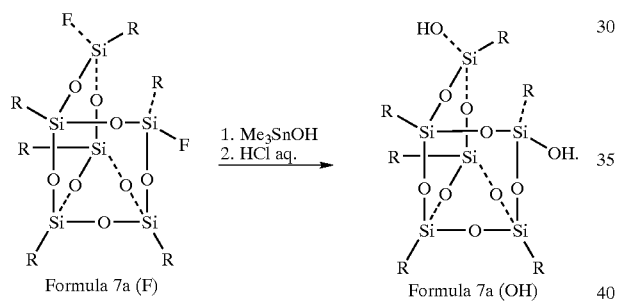
Formula 7a (F)   Formula 7a (OH)
8. The method of claim 1 wherein
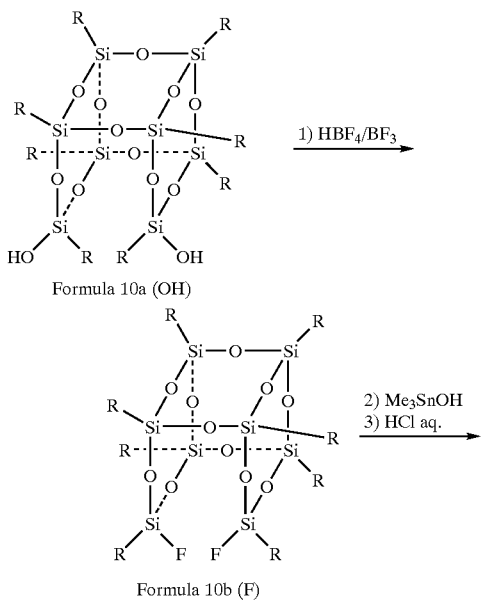
Formula 10a (OH)
Formula 10b (F)
9. The method of claim 1 wherein
Formula 7a (OH)
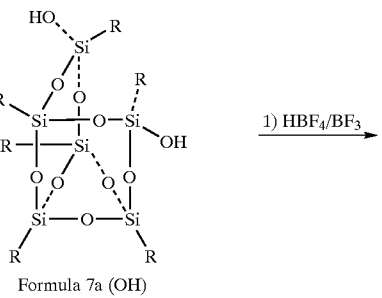
Formula 7b (F)   Formula 7b (OH)
10. The method of claim 1 wherein
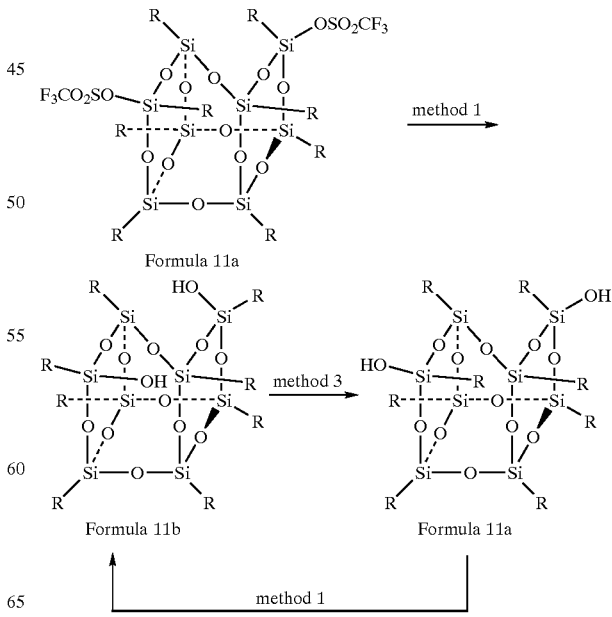
Formula 11a
Formula 11b   Formula 11a where method 1 is the hydrolysis of $OSO_2CF_3$ groups to a silanol species with inversion of stereochemistry as described in claim 1a) and method 3 is the stereochemical change of position of OH groups as described in claim 1c).

11. A polyhedral oligomeric silsesquioxane (POSS) stereo compound of the formula $[(RSiO_{1.5})_m(RXSiO_{1.0})_n]_{\Sigma\#}$ where m=4–24, n=1–12, #=m+n, R is aliphatic, aromatic, olefinic, alkoxy, siloxy or H and X is selected from the group consisting of $OSO_2$, $CF_3$, $OSO_2$, $CH_3$, F, Cl, I, Br, alkoxy and siloxy and Σ=nanostructure.

12. A POSS compound selected from the group consisting of all formulas 7, 10 & 11 and all a, b, c variants thereof shown in claims 3–10.

13. The POSS compound of claim 11 selected from the group of difunctional incompletely condensed $[(RSiO_{1.5})_4 (RXSiO_{1.0})_2]_{\Sigma 6}$, tetrafunctional twisted $[(RSiO_{1.5})_2 (RXSiO_{1.0})_4]_{\Sigma 6}$, tetrafunctional incompletely condensed $[(RSiO_{1.5})_2(RXSiO_{1.0})_4]_{\Sigma 6}$, difunctional twisted $[(RSiO_{1.5})_6 (RXSiO_{1.0})_2]_{\Sigma 8}$, difunctional $[(RSiO_{1.5})_5(R^3SiO_{1.5})_1 (RXSiO_{1.0})_2]_{\Sigma 8}$ and their isomers where $R^3$ is selected from the same group as R but different from at least one R.

14. A method for inserting a ring substituent into a polyhedral oligomeric silsesquioxane (POSS) compound comprising, reacting $[(RSiO_{1.5})_m(RXSiO_{1.0})_n]_{\Sigma\#}$, with a reagent selected from the group of $H_2NR$, $RB(OH)_2$, $K_2CrO_4$, $R_4NHSO_4$, and $H_2PR$ to obtain at least one expanded POSS ring of $[(RSiO_{1.5})_m(RSiO_{1.0})_n(E)_j]_{\Sigma\#}$, where n is n is 1, 2 & 4–24, m is 1–12, j is 1–8, # is m+n+j, R is aliphatic, aromatic, olefinic, alkoxy, siloxy or H, X is selected from the group consisting of $OSO_2CF_3$, $OSNMe_3$, OH, $OSO_2Cl$, $OSO_2CH_3$, $OSO_3H$, amine, and halide and E is a ring substituent replacement for oxygen selected from the group consisting of NR, PR, $CrO_4$, $SO_4$, $O_2BR$, $O_2PR$ and $O_2P(O)R$ and Σ=nanostructure.

15. The method of claim 14 wherein R is selected from the group of alkyl, vinyl, allyl and phenyl and X is a halide or an amine selected from the group of $NH_2$, NHR and $NR_2$.

16. The method of claim 14 wherein

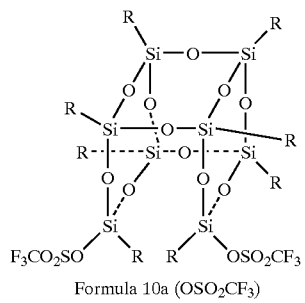

Formula 10a ($OSO_2CF_3$)

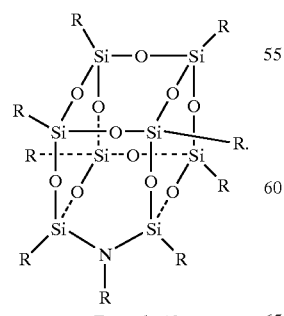

Formula 19

17. The method of claim 14 wherein

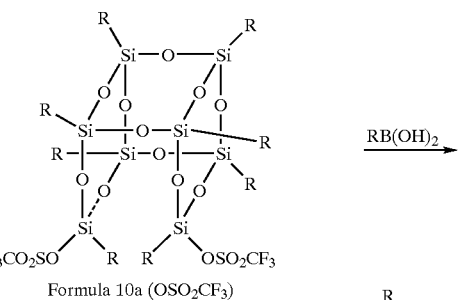

Formula 10a ($OSO_2CF_3$)

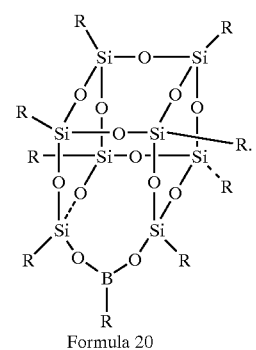

Formula 20

18. The method of claim 14 wherein

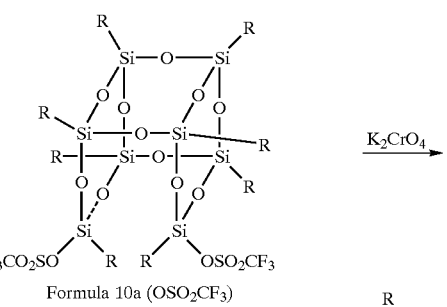

Formula 10a ($OSO_2CF_3$)

Formula 21a

19. The method of claim 14 wherein

Formula 10a ($OSO_2CF_3$)

-continued

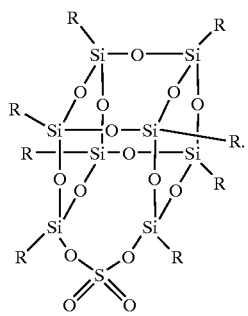

Formula 21b

20. A composition having at least one expanded ring in polyhedral oligomeric silsesquioxane (POSS) of the formula $[(RSiO_{1.5})_m(RSiO_{1.0})_n(E)_j]_{\Sigma\#}$, where # is m+n+j, R is aliphatic, aromatic, olefinic, alkoxy, siloxy or H, m is 1–12, n is 4–24, j is 1–8 and E is a ring substituent replacement for oxygen selected from the group of NR, PR, $CrO_4$, $SO_4$, $O_2BR$, $O_2PR$ and $O_2P(O)R$ and $\Sigma$=nanostructure.

21. The composition selected from the group consisting of formulas 19, 20 and 21 a & b shown in claims 16–19.

* * * * *